(12) United States Patent
Hielscher et al.

(10) Patent No.: US 10,111,594 B2
(45) Date of Patent: Oct. 30, 2018

(54) COMPACT OPTICAL IMAGING DEVICES, SYSTEMS, AND METHODS

(71) Applicant: The Trustees of Columbia University in the City of New York, New York, NY (US)

(72) Inventors: Andreas H. Hielscher, Brooklyn, NY (US); Molly L. Flexman, New York, NY (US); Ronny Stoll, Hamburg (DE); Hyun K. Kim, Cresskill, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 898 days.

(21) Appl. No.: 14/348,081

(22) PCT Filed: Sep. 28, 2012

(86) PCT No.: PCT/US2012/058065
§ 371 (c)(1),
(2) Date: Mar. 28, 2014

(87) PCT Pub. No.: WO2013/049677
PCT Pub. Date: Apr. 4, 2013

(65) Prior Publication Data
US 2014/0243681 A1    Aug. 28, 2014

Related U.S. Application Data

(60) Provisional application No. 61/541,488, filed on Sep. 30, 2011.

(51) Int. Cl.
*A61B 5/00* (2006.01)
*A61B 5/145* (2006.01)
*A61B 5/1455* (2006.01)

(52) U.S. Cl.
CPC ........ *A61B 5/0075* (2013.01); *A61B 5/0002* (2013.01); *A61B 5/0073* (2013.01);
(Continued)

(58) Field of Classification Search
None
See application file for complete search history.

(56) References Cited

U.S. PATENT DOCUMENTS 5,337,745 A * 8/1994 Benaron ............... A61B 5/1455
356/39
5,676,143 A    10/1997 Simonsen et al.
(Continued)

FOREIGN PATENT DOCUMENTS

EP    0797916 A1    10/1997

OTHER PUBLICATIONS

International Search Report and Written Opinion for International Application No. PCT/US2012/058065.
(Continued)

*Primary Examiner* — Katherine Fernandez
*Assistant Examiner* — Bradley Impink
(74) *Attorney, Agent, or Firm* — Potomac Law Group, PLLC; Mark A. Catan

(57) ABSTRACT

An optical imaging device and system can be used to visualize and/or provide a quantitative measure of changes in patient vasculature, for example, to monitor responsiveness of a tumor to a particular chemotherapy treatment. A plurality of detectors (e.g., two) are spaced from a plurality of substantially monochromatic light sources (e.g., four) on an interrogation face of the handheld device. Wavelengths of light in the near-infrared range are used to measure the content of hemoglobin, water, and lipid of the tissue that the interrogation face comes in contact with. The light can be modulated so that the effect of ambient light is not mini-
(Continued)

mized or at least reduced. The detected signal is amplified, filtered, and digitized within the device by appropriate electronics. In embodiments, handheld device can include a wireless communication module, such as a Bluetooth device, for wireless transmission of data to/from the remote processor or computer.

17 Claims, 10 Drawing Sheets

(52) U.S. Cl.
CPC .......... *A61B 5/6803* (2013.01); *A61B 5/6807* (2013.01); *A61B 5/6843* (2013.01); *A61B 5/7228* (2013.01); *A61B 5/0091* (2013.01); *A61B 5/1455* (2013.01); *A61B 5/14546* (2013.01); *A61B 2560/0443* (2013.01); *A61B 2560/0456* (2013.01); *A61B 2562/0238* (2013.01); *A61B 2562/043* (2013.01); *A61B 2562/08* (2013.01); *A61B 2562/164* (2013.01); *A61B 2562/168* (2013.01)

(56) References Cited

U.S. PATENT DOCUMENTS

| | | | |
|---|---|---|---|
| 7,627,365 B2 | 12/2009 | Chance | |
| 7,884,933 B1 | 2/2011 | Kashyap et al. | |
| 2001/0032053 A1 | 10/2001 | Hielscher et al. | |
| 2004/0030255 A1 | 2/2004 | Alfano et al. | |
| 2004/0152976 A1* | 8/2004 | Hengerer | A61B 5/0091 600/431 |
| 2006/0253007 A1 | 11/2006 | Cheng et al. | |
| 2007/0038122 A1 | 2/2007 | Geng | |
| 2008/0232653 A1 | 9/2008 | Rowe | |
| 2009/0240138 A1 | 9/2009 | Yi | |
| 2010/0010340 A1* | 1/2010 | Godavarty | A61B 5/0091 600/425 |
| 2010/0331707 A1 | 12/2010 | Fukutani et al. | |
| 2011/0273165 A1* | 11/2011 | Palassis | G01D 11/00 324/149 |
| 2012/0179037 A1* | 7/2012 | Halmann | A61B 8/4427 600/443 |

OTHER PUBLICATIONS

Klose et al., Investigations of RA-Diagnostics applying Optical Tomography in frequency-domain. SPIE vol. 3196, 1998.
Kirkby, David "[time-nuts] Phase noise with a lock-in amplifier," Apr. 16, 2005, XP055168055, Retrieved from the Internet: URL:https://www.febo.com/pipermail/time-nuts/2005-April/018073.htm] [retrieved on Feb. 6, 2015], p. 3.
Armen, Dr. G. Bradley "Phase sensitive detection: the lock-in amplifier," Apr. 1, 2008, XP055168076, Retrieved from the Internet: URL:http://www.phys.utk.edu/labs/modphys/1ock-in_amplifier_experiment.pdf [retrieved on Feb. 6, 2015], pp. 1, 4, 19.
Supplementary European Search Report dated Mar. 20, 2015, in corresponding European Application No. EP 12 83 5602.
Office Action for European Patent Application No. 12835602.9 dated Mar. 2, 2016.
Office Action for European Patent Application No. 12835602.9 dated Nov. 29, 2016 regarding third party observations.
Atsumori et al., "Development of wearable optical topography system for mapping the prefrontal cortex activation," Review of Scientific Instruments, Apr. 2009, vol. 80(4), pp. 043704-1-043704-6.

Brown et al., "Characterization of early stage cartilage degradation using diffuse reflectance near infrared spectroscopy," Physics in Medicine and Biology, Mar. 2011, vol. 56(7), pp. 2299-2307.
Cerussi et al., "In vivo absorption, scattering, and physiologic properties of 58 malignant breast tumors determined by broadband diffuse optical spectroscopy," Journal of Biomedical Optics, Jul./Aug. 2006, vol. 11(4), pp. 044005-1-044005-16.
Doombos et al., "The determination of in vivo human tissue optical properties and absolute chromophore concentrations using spatially resolved steady-state diffuse reflectance spectroscopy," Physics in Medicine and Biology, Apr. 1999, vol. 44(4), pp. 967-981.
Durduran et al., "Diffuse optics for tissue monitoring and tomography," Reports on Progress in Physics, Jun. 2, 2010, 076701, vol. 73(7), (43 pages).
Farrell et al., "A diffusion theory model of spatially resolved, steady-state diffuse reflectance for the noninvasive determination of tissue optical properties in vivo," Medical Physics, Jul./Aug. 1992, vol. 19(4), pp. 879-888.
Farrell et al., "The use of a neural network to determine tissue optical properties from spatially resolved diffuse reflectance measurements," Physics in Medicine and Biology, Dec. 1992, vol. 37(12), pp. 2281-2286.
Flexman et al., "Digital optical tomography system for dynamic breast imaging," Journal of Biomedical Optics, Jul. 2011, vol. 16(7), pp. 076014-1-076014-16.
Ge et al., "Three-dimensional fluorescence-enhanced optical tomography using a hand-held probe based imaging system," Medical Physics, Jul. 2008, vol. 35(7), pp. 3354-3363.
Kang et al., "Application of novel dynamic optical imaging for evaluation of peripheral tissue perfusion," International Journal of Cardiology, Dec. 3, 2010, vol. 145(3), pp. e99-e101.
Keijzer et al., "Optical diffusion in layered media," Applied Optics, May 1, 1988, vol. 27(9), pp. 1820-1824.
Kfouri et al., "Toward a miniaturized wireless fluorescence-based diagnostic imaging system," IEEE Journal of Selected Topics in Quantum Electronics, Jan./Feb. 2008, vol. 14(1), pp. 226-234.
Kim et al., "PDE-constrained multispectral imaging of tissue chromophores with the equation of radiative transfer," Biomedical Optics Express, Oct. 1, 2010, vol. 1(3), pp. 812-824.
Lasker et al., "Digital-signal-processor-based dynamic imaging system for optical tomography," Review of Scientific Instruments, Aug. 2007, vol. 78(8), pp. 083706-1-083706-19.
Muehlemann et al., "Wireless miniaturized in-vivo near infrared imaging," Optics Express, Jul. 7, 2008, vol. 16(14), pp. 10323-10330.
Office Action for European Patent Application No. 12835602.9 dated Dec. 5, 2017.
Patterson et al., "Time resolved reflectance and transmittance for the noninvasive measurement of tissue optical properties," Applied Optics, Jun. 15, 1989, vol. 28(12), pp. 2331-2336.
Tromberg et al., "Assessing the future of diffuse optical imaging technologies for breast cancer management," Medical Physics, Jun. 2008, vol. 35(6), pp. 2443-2451.
Wang et al., Wireless spectroscopic compact photonic explorer for diagnostic optical imaging, Biomedical Microdevices, Jun. 1, 2005, vol. 7(2), pp. 111-115.
Xu et al., "A prospective pilot clinical trial evaluating the utility of a dynamic near-infrared imaging device for characterizing suspicious breast lesions," Breast Cancer Research, Dec. 18, 2007, vol. 9(6), R88 (12 pages).
Xu et al., "Development of a handheld near infrared imager for dynamic characterization of in vivo biological tissue systems," Applied Optics, Oct. 20, 2007, vol. 46(30), pp. 7442-7451.
Zhu et al., "Optimal probing of optical contrast of breast lesions of different size located at different depths by US localization," Technology in Cancer Research & Treatment, Aug. 2006, vol. 5(4), pp. 365-380.

* cited by examiner

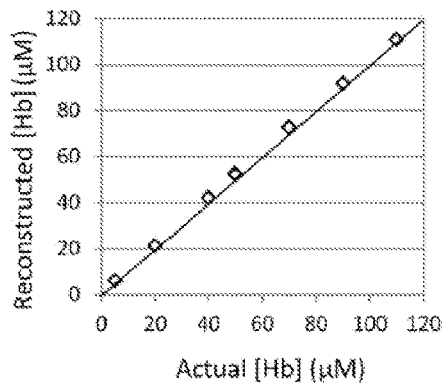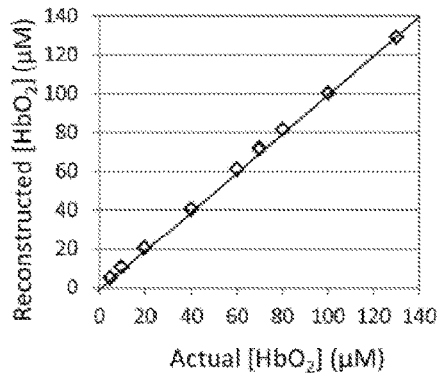
FIG. 6A  FIG. 6B
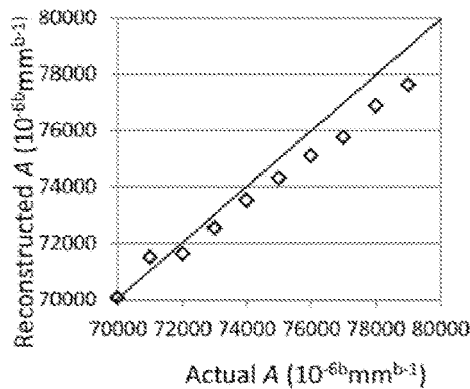
FIG. 6C  FIG. 7C
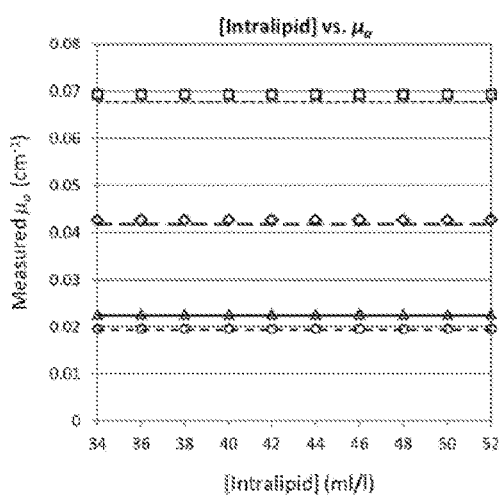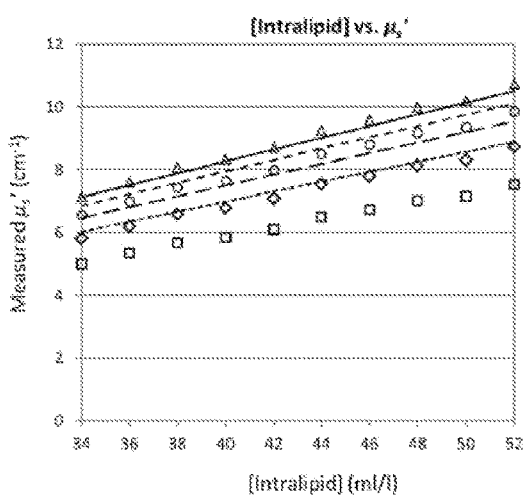
FIG. 7A  FIG. 7B

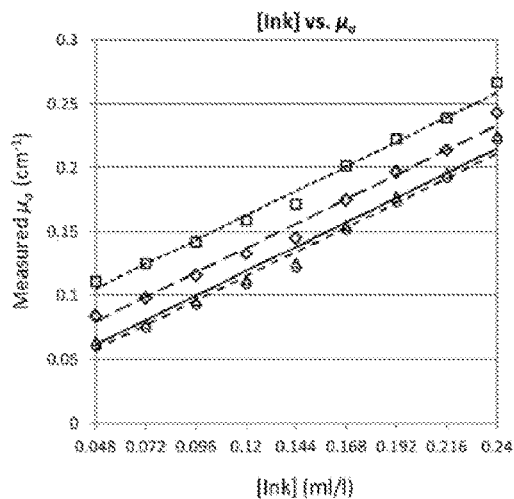
FIG. 8A
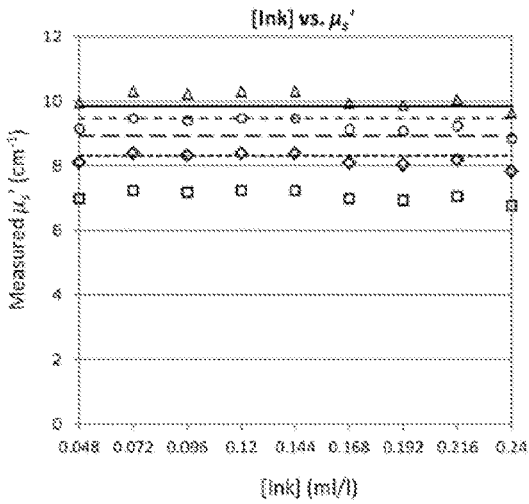
FIG. 8B
FIG. 8C
FIG. 9C
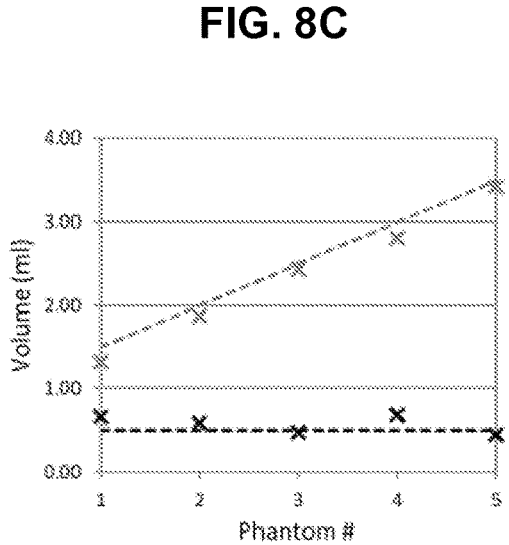
FIG. 9A
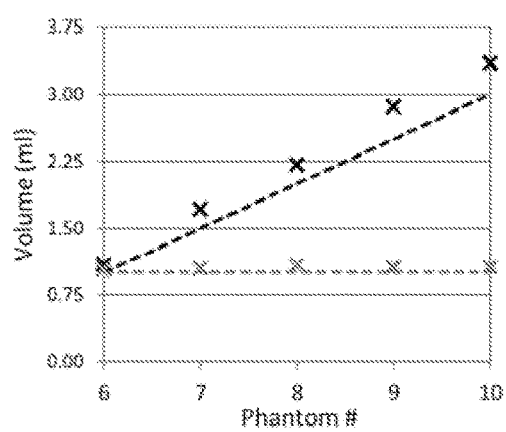
FIG. 9B

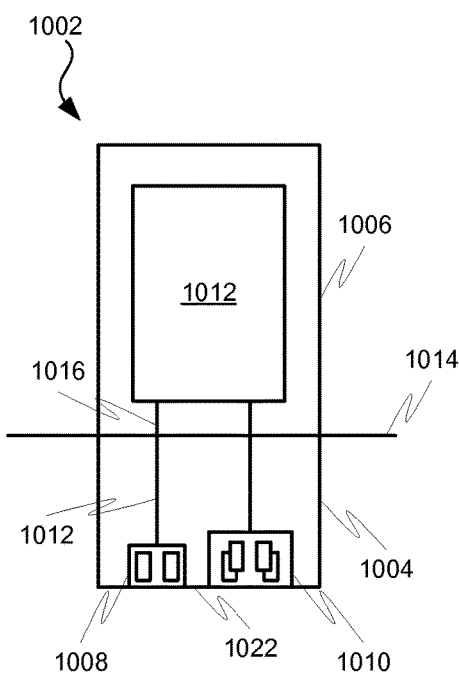
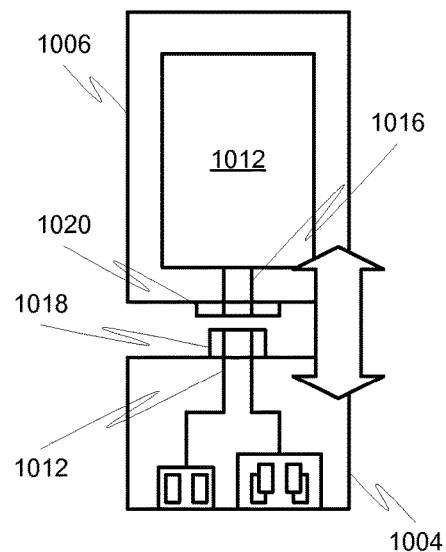
FIG. 11A  FIG. 11B
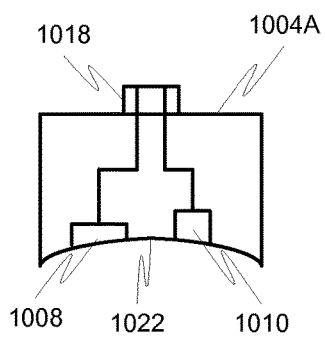 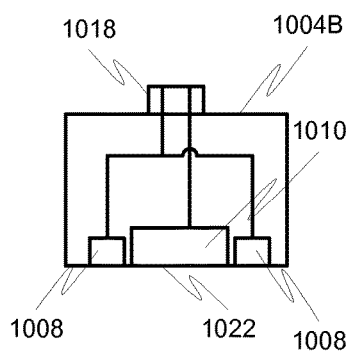 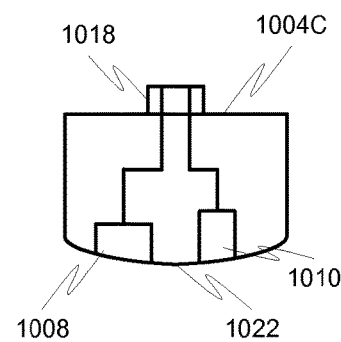
FIG. 12A  FIG. 13A  FIG. 14A
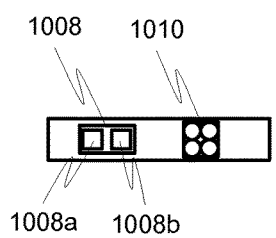 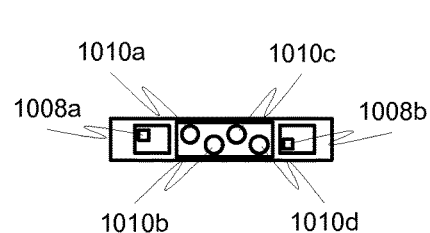 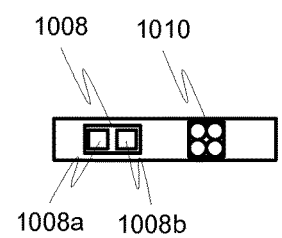
FIG. 12B  FIG. 13B  FIG. 14B

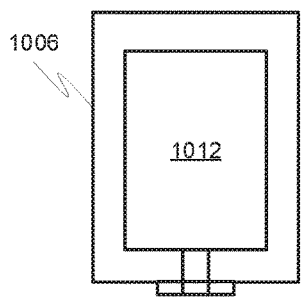
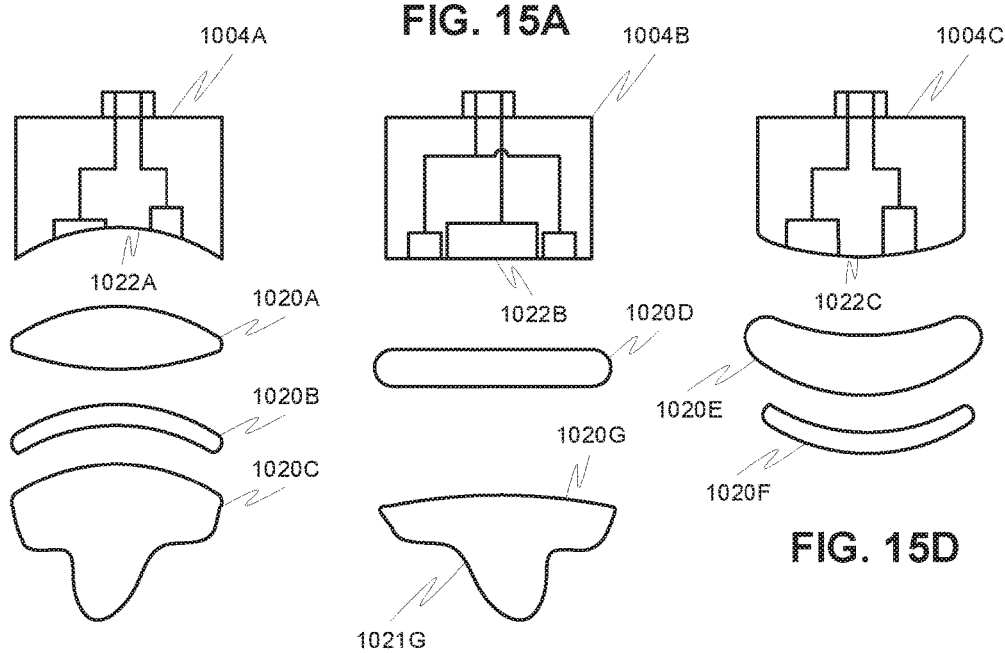
FIG. 15A
FIG. 15B  FIG. 15C  FIG. 15D
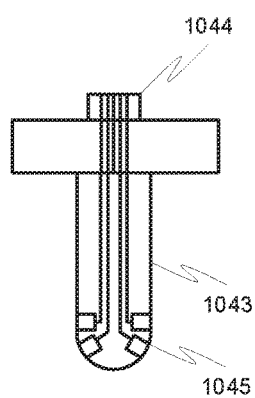
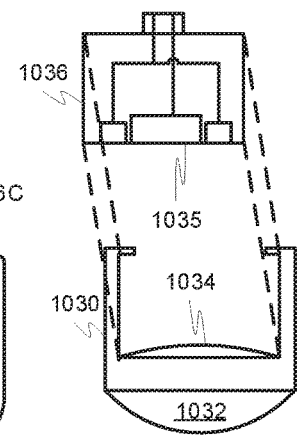
FIG. 15E  FIG. 15F

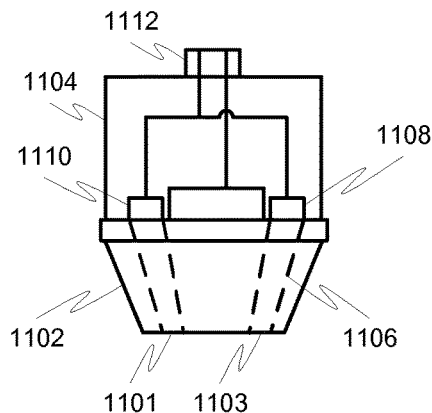
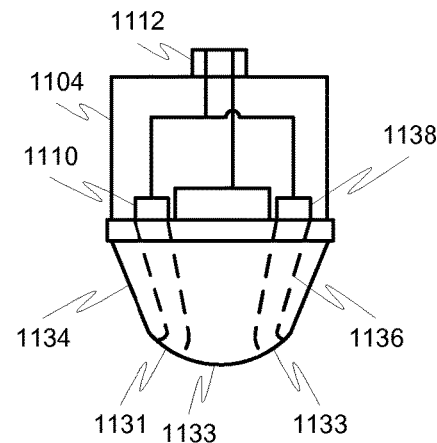
Fig. 16A　　　　　　　　　　Fig. 16B
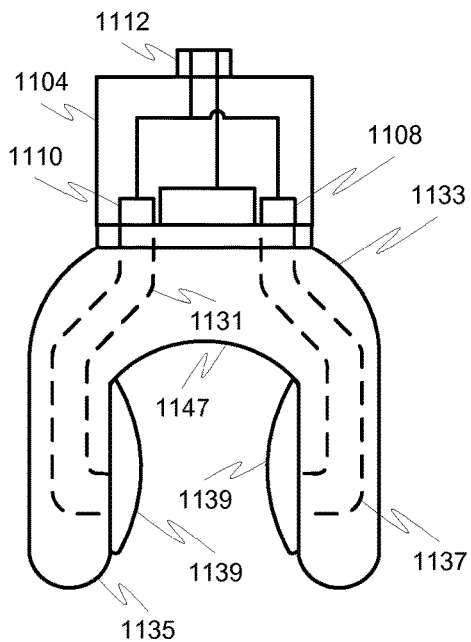
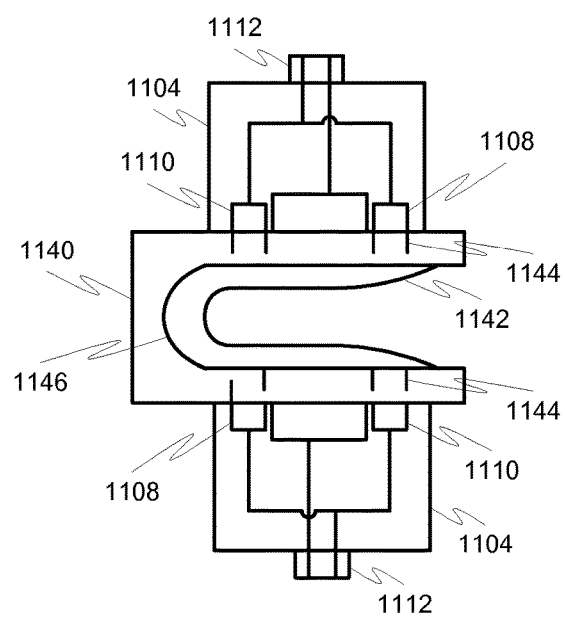
Fig. 17A　　　　　　　　　　Fig. 17B
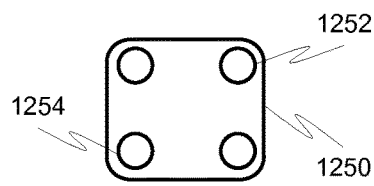
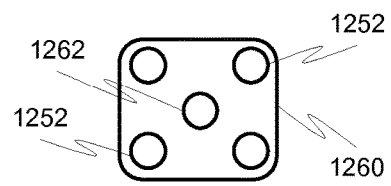
Fig. 18A　　　　　　　　　　Fig. 18B

COMPACT OPTICAL IMAGING DEVICES, SYSTEMS, AND METHODS

CROSS-REFERENCE TO RELATED APPLICATIONS

The present application claims the benefit of U.S. Provisional Application No. 61/541,488, filed Sep. 30, 2011, which is hereby incorporated by reference herein in its entirety.

STATEMENT REGARDING FEDERALLY SPONSORED RESEARCH

This invention was made with Government support under grants CA118666 and CA126513 awarded by the National Institutes of Health. The Government has certain rights in the invention.

FIELD

The present disclosure relates generally to optical imaging of tissue, and, more particularly, to compact optical imaging with spectrally constrained evolution strategies for diffuse optical imaging of tissue.

BACKGROUND

Breast cancer affects approximately 1 in 8 women in the United States and the incidence of breast cancer throughout the world is increasing. With more than 200,000 new cases every year, it accounts for 28% of all new cancers diagnosed in women, with almost 40,000 deaths caused by breast cancer each year in the US. Ultrasound, magnetic resonance imaging (MRI) and/or X-ray imaging are currently used for breast tumor detection.

For advanced breast tumors, the patient may undergo neoadjuvant chemotherapy (NACT) prior to surgery to improve outcomes, provide the option for breast-conserving surgery, and improve surgical margins. However, only 8-15% of patients have a complete pathological response to NACT. Currently, the success of NACT treatment can only be assessed through palpation or MRI imaging at the beginning and end of the NACT treatment. Thus, patients will have to undergo weeks of NACT treatment without knowing if the treatment is effective and for many of these patients NACT treatment will be ineffective.

SUMMARY

A handheld optical imaging device can be used to visualize and/or provide a quantitative measure of changes in patient vasculature, for example, to monitor responsiveness of a tumor to a particular chemotherapy treatment. The handheld optical imaging device can include a plurality of detectors (e.g., two) spaced from a plurality of substantially monochromatic light sources (e.g., four) on an interrogation face of the handheld device. The device can use light, for example wavelengths of light in the near-infrared range, to measure the quantity of hemoglobin, water, and lipid of the tissue with which the interrogation face comes in contact. The absolute quantity of these fractions or their relative quantities or changes in quantities may be measured. The light can be modulated so that the effect of ambient light is reduced. The detected signal can be amplified, filtered, and digitized within the device by appropriate electronics. Raw signal data can be partially reduced in a portable terminal, such as a hand-held scanning device, and further reduced by a remote system, which may be a multifunction computer such as a laptop or an embedded system. The remote system may render synthetic displays to represent the data in various ways that are known for optical tomographic data, such as representational images such as color maps. In an embodiment of a handheld device, a wireless communication channel providing communication with the remote system may be employed, such as a Bluetooth, to allow the handheld device to facilitate use.

The wireless handheld probe is low-cost, portable, and provides the well-known benefits of optical tomographic systems. Among the benefits are suitability for screening applications or in situations such as NACT, where multiple serial measurements over time can improve patient outcomes. In addition, to monitoring therapy effects, this device may also be useful for front line screening for breast cancer. The portability and simplicity of the handheld probe can make it useful to primary-care physicians, in low resource settings, and/or to supplement X-ray mammography.

In embodiments, a method for quantifying light absorbable materials in a medium can include illuminating a surface of the medium with multi-spectral continuous wave optical radiation and detecting optical radiation from the medium surface. The method can further include, using one or more processors, calculating at least one absolute quantifiable parameter of the medium using a correlation between measured spatially-resolved reflectance based on the detected optical radiation and predicted spatially-resolved reflectance based on the at least one quantifiable parameter. The at least one quantifiable parameter can include a concentration of one of the light absorbable materials. A system can include a handheld wireless probe and a wirelessly attached host processor. The host processor can be configured to execute a method including said calculating. The probe and the host processor, in combination, can be configured to execute the method.

In embodiments, a compact optical imaging system includes an imaging probe. The imaging probe can have a plurality of illumination sources and a plurality of detectors disposed on an interrogation face of the probe. The detectors can be spaced from each other on the interrogation face. The plurality of illumination sources can be disposed at respective illumination locations spaced from each other and the detection locations on the interrogation face. The plurality of illumination sources can emit substantially monochromatic light. The interrogation face can be configured to be brought into contact with an object to be imaged such that light from the light sources is scattered and/or partially absorbed by the object prior to detection by one or more of the plurality of detectors.

In embodiments, a method of imaging using a compact optical imaging system can include providing an imaging probe in contact with an object to be imaged. The imaging probe can have a plurality of illumination sources and a plurality of detectors disposed on an interrogation face of the probe. The detectors can be disposed at respective detection locations spaced from each other on the interrogation face. The illumination sources can be disposed at respective illumination locations spaced from each other and the detection locations on the interrogation face. The method can further include illuminating the object with light from each illumination source such that the light is scattered and/or partially absorbed by the object. The method can also include detecting the scattered and/or partially absorbed light with at least one of the plurality of detectors. Responsively to signals from the detectors indicative of the detected light, at least one of at least one of absorption, scattering, and chromophore concentration can be quantitatively determined by a remote processor.

In embodiments, a method for monitoring efficacy of a patient treatment using the compact optical imaging system can include interrogating a portion of the patient using the imaging probe by illuminating the patient with NIR light from the illumination sources and detecting at the detectors light scattered and/or partially absorbed by the patient. Responsively to signals from the detectors indicative of the detected light, at least one of at least one of absorption, scattering, and chromophore concentration for the portion of the patient can be quantitatively determined by using a remote processor. The method can further include administering a treatment to the patient, and repeating the interrogating and the determining.

In embodiments, a compact optical imaging system having an imaging probe body and a plurality of imaging probe heads. Each imaging probe head can have a plurality of illumination sources and detectors and a connector. The plurality of illumination sources and detectors can be disposed at different locations from each other on an interrogation face of said probe head. The connector can be for detachably interfacing with the imaging probe body. The imaging probe body can include a processor therein for controlling the illumination sources and processing signals from the detectors of one of the imaging probe heads connected thereto. The interrogation face of each of the plurality of imaging probe heads can be different from others of the imaging probe heads with respect to at least one of layout of detectors on the interrogation face, layout of illumination sources on the interrogation face, shape or curvature of the interrogation face, number of detectors, and number of illumination sources.

In embodiments, a handheld wireless optical imaging probe can include a plurality of light sources, a plurality of detectors, a processing device, and a wireless communication device. The plurality of light sources can illuminate a sample with near-infrared light. The plurality of detectors can receive light scattered while passing through the sample. The processing device can be in communication with the plurality of detectors and can determine absolute values for optical properties of the sample based on signals received from the plurality of detectors. The wireless communication device can transfer measurement data to a remote device.

In embodiments, a wireless optical imaging method for performing diffuse optical sample measurement can include contacting a sample with a compact wireless imaging probe having a plurality of near-infrared illumination sources, a plurality of light detection devices, a processing device, and a wireless communication device. The method can further include illuminating the sample with near-infrared light having a plurality of wavelengths, and detecting light which scatters while passing through the sample. The method can also include applying a multispectral evolution algorithm to determine actual absolute optical parameters from the detected light signals, and transmitting the determined optical parameters wirelessly to a remote device.

In embodiments, an optical tomography kit can include a probe unit, a first probe head, and at least two optically transmissive adapters. The probe unit can have processing components for raw signal data reduction and transmission to a processor that generates an optical tomographic image from demodulated optical data received from the probe unit. The first probe head can have at least one optical source and at least one optical detector. The at least two optically transmissive adapters can each be configured to attach to the first probe head over the at least one optical source and the at least one optical detector to permit light to pass therethrough. Each of the adapters can also have a different respective size or shape from a size or shape of the other.

In embodiments, an optical tomography kit can include a probe unit, a first probe head, and a second probe head. The probe unit can have processing components for raw signal data reduction and transmission to a processor that generates an optical tomographic image from demodulated optical data received from the probe unit. The first and second probe heads can each have at least one optical source and at least one optical detector that receive and transmit light through a respective interrogation face thereof. The first probe head interrogation face can have a different shape or size from the second probe head interrogation face.

In embodiments, an optical tomography kit can include a probe unit, a first probe head, and a second probe head. The probe unit can have processing components for raw signal data reduction and transmission to a processor that generates an optical tomographic image from demodulated optical data received from the probe unit. The first probe head and the second probe head can each have at least one optical source and at least one optical detector that receive and transmit light through a respective interrogation face thereof. For the first probe head interrogation face, the spacing or arrangement of the at least one optical detector and the at least one optical source, or the directions in which the at least one optical source and the at least one optical detector face can differ from each other.

In embodiments, an optical tomography kit can include a probe unit, a first probe head, and at least two optically transmissive adapters. The probe unit can have processing components for raw signal data reduction and transmission to a processor that generates an optical tomographic image from demodulated optical data received from the probe unit. The first probe head can have at least one optical source and at least one optical detector. The least two optically transmissive adapters can each be configured to attach to the first probe head over the at least one optical source and the at least one optical detector to permit light to pass therethrough. Each of the adapters can have at least one light guide element that positions or directs light from or to at least one of the at least one optical source and at least one optical detector to a different position or a different location than the other.

In embodiments, a method for generating an optical tomographic image can include selecting a first spacing between the optical source and the optical detector of an optical tomography probe by selecting an adapter from a kit of adapters having different spacings and attaching a first selected one to the probe and generating an image with said probe. The method can further include selecting a second spacing between the optical source and the optical detector of an optical tomography probe by selecting a second adapter from a kit of adapters having different spacings and attaching the second selected one to the probe and generating an image with said probe.

In embodiments, a method for generating an optical tomographic image can include selecting a first spacing between the optical source and the optical detector of an optical tomography probe by selecting an adapter from a kit of adapters having different configurations. The method can also include attaching a first selected one to the probe and generating an image with said probe. The method can also include selecting a second configuration of the optical source and the optical detector of an optical tomography probe by selecting a second adapter from a kit of adapters having different spacings. The method can further include attaching the second selected one to the probe and generating an image with said probe.

In embodiments, an optical tomographic imaging apparatus can include at least two modular probes. Each of the probes can have at least one optical source, at least one optical detector, and processing unit. The processing unit can be configured to demodulate raw optical signals received by respective ones of said at least one optical source and to generate an output signal responsive thereto. Each of the probes can be substantially identical and connected for signal transmission to a processor configured to receive and generate images from a respective one of the output signals. The output signal from each of the respective modular probes can be sufficient to generate an image therefrom. The processor can be configured to control the imaging probes such that light from the source of one of the at least two probes is received by the detector of the other of the at least two probes according to a first imaging sequence definition stored in the processor. The processor can be configured to control the imaging probes such that light from the source of one of the at least two probes is received by the detector of the same one of the at least two probes according to a second imaging sequence definition stored in the processor.

In embodiments, a multispectral evolutionary algorithm can determine actual absolute values for optical tissue parameters based on absorption and scattering data extracted by probing the tissue in vivo using near infrared light. Such tissue parameters can include scattering amplitude and oxygenated and deoxygenated tissue hemoglobin concentrations.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIGS. 6A-6C are graphs of reconstructed values of Hb, $HbO_2$, and A, respectively, versus the actual values expected for various cases using a numerical phantom.

FIGS. 7A-7B are graphs of reconstructed values of $\mu_a$ and $\mu_s'$, respectively for linearly increasing amounts of Intralipid® added to a phantom.

FIG. 7C is the legend for the graphs of FIGS. 7A-7B, where 780, 808, 850, and 904 refer to the respective wavelengths of light used in nanometers (nm).

FIGS. 8A-8B are graphs of reconstructed values of $\mu_a$ and $\mu_s'$, respectively, for linearly increasing amounts of ink added to a phantom.

FIG. 8C is the legend for the graphs of FIGS. 8A-8B, where 780, 808, 850, and 904 refer to the respective wavelengths of light used in nanometers (nm).

FIGS. 9A-9B are graphs of reconstructed volumes of ink (grey line) and dye (black line) in an Intralipid® solution for linearly increasing amounts of ink and linearly increasing amounts of dye, respectively.

FIG. 9C is the legend for the graphs of FIGS. 9A-9B, where the grey line/markers represent ink and the black line/markers represent dye.

FIGS. 11A-11B shows a handheld imaging probe with removable/interchangeable imaging head, according to one or more embodiments of the disclosed subject matter.

FIGS. 12A, 13A, and 14A show various configurations for an imaging head for use with the handheld imaging probe of FIGS. 11A-11B, according to one or more embodiments of the disclosed subject matter.

FIGS. 12B, 13B, and 14B show the layout of detection and illumination components on the interrogation face of the imaging heads of FIGS. 12A, 13A, and 14A, respectively, according to one or more embodiments of the disclosed subject matter.

FIGS. 15A through 15F illustrate adapter configurations for modifying the function of a handheld wireless imaging device, according to further embodiments of the disclosed subject matter.

FIGS. 16A and 16B illustrate light guide embodiments that modify the function of a handheld wireless imaging device, according to further embodiments of the disclosed subject matter.

FIGS. 17A and 17B illustrate light guide embodiments that provide transmission and multi-angle interrogation using handheld wireless imaging device, according to further embodiments of the disclosed subject matter.

FIGS. 18A and 18B show alternative layouts of sources and detectors according to embodiments of the disclosed subject matter.

DETAILED DESCRIPTION

Diffuse optical imaging (DOI) uses light, for example, near-infrared (NIR) light, to probe tissue in vivo and to extract information about the absorption and scattering. Tissue absorption in the NIR is primarily affected by the concentration of oxy- and deoxy-hemoglobin, lipid and water. By providing information on the hemoglobin, water, and fat content of tissue, optical imaging can provide physiological information that complements or supplants anatomical information shown in X-ray mammography, ultrasound, and/or MRI. In addition, the costs associated with DOI are generally much lower than other imaging modalities. DOI uses non-ionizing radiation (e.g., near infrared radiation) and thus presents no harmful effects from repeated exposure.

DOI is therefore an ideal modality for frequent imaging of a patient, for example, to monitor a patient during chemotherapy treatment. These properties make optical measurements well suited to a variety of clinical applications including breast cancer, functional brain imaging, and peripheral artery disease. Such imaging techniques can be used to monitor patient progress frequently, especially early on in the treatment schedule, or to detect tumors by relying on visualization of vascular changes, as opposed to anatomical changes relied on by other modalities, such as X-ray, ultrasound, and magnetic resonance imaging (MRI). This ability to monitor individual patient response to therapy can provide optimized drug selection, timing, and reduce both cost and toxicity while improving patient outcomes.

In embodiments of the disclosed subject matter, an optical imaging probe is used to perform diffuse optical tissue measurements with absolute reconstruction of the concentrations of tissue chromophores, including the contribution of tissue scattering. For example, the imaging device may be used to monitor breast cancer and/or tumor response to treatment. The probe may include a wired or wireless communication module such that data acquired by the probe can be transmitted to remote terminal for further processing or viewing by a user. In addition, a multi-spectral genetic/evolution algorithm as disclosed herein may be used to measure absolute values (as opposed to a relative value) of at least one of scattering amplitudes and concentrations of oxy- and deoxy hemoglobin in the patient.

Figure 1:
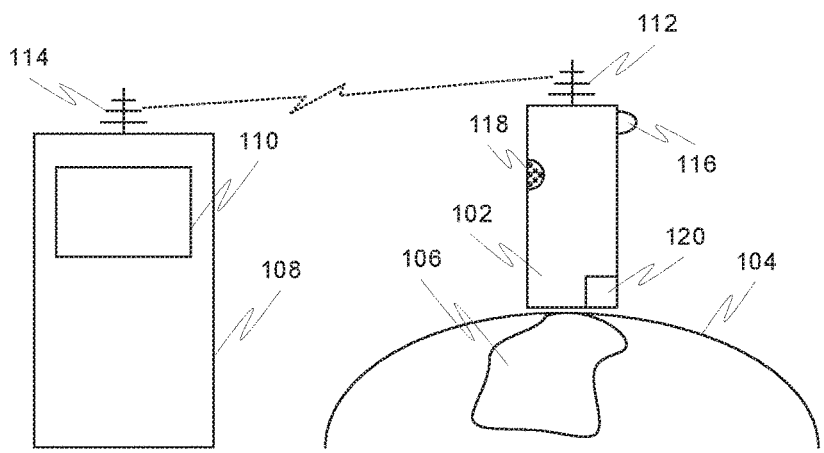
FIG. 1 shows the use of a handheld imaging device for monitoring a tumor within a patient, according to one or more embodiments of the disclosed subject matter.

Referring to FIG. 1, an optical imaging system may be used for interrogating the tissue of a patient, a body part of which is indicated at 104. An imaging probe 102 illuminates an underlying tissue volume of the patient body part 104, which, in the present example, includes a substructure or feature such as a tumor or 106 (or any other anatomical or histological structure or phenomenon to be interrogated). Probe 102 is sized and shaped so to permit convenient manipulation by hand. For example, it may be light enough to be held in a single hand of a user. Under manipulation, it may be moved progressively across, or held in position, on the skin of the patient body part 104 or the surface of an organ of the patient. Different regions 106 can be monitored by moving the probe 102 across the patient. The probe 102 may be configured for direct contact with the patient as illustrated. In alternative embodiments, the probe may be configured with suitable optics such that it can generate data without contacting the patient at all. For example, by providing a laser as a source of illumination or precise optics for focusing light on a target area, and with imaging optics, the scattered light may be captured without making contact with the patient. In other embodiments, the surface that makes contact with the patient may be provided with a suitable interface material such as a gel or fluid filled bladder as known in the art.

In embodiments where intimate contact of the probe interrogation surface and the tissue surface is desirable or necessary, the probe 102 can include a contact sensing module 120, which provides an indication of whether the interrogation surface of the probe 102 is in contact with the patient 104. For example, the contact sensing module 120 can be an optical, acoustic, pressure sensing, temperature sensing, or conductivity sensing device. Alternatively or additionally, either a remote processor (e.g., associated with terminal 108) or a processor internal to the probe 102 can be configured to compute whether there is good contact between the tissue 104 and the interrogation surface of the probe 102 based on the amplitude and/or characteristics of the detected optical signals (e.g., light from illumination source 204 detected by detector 202 in FIG. 2).

For example, the quality of contact made between the tissue 104 and the probe 102 can be computed based on the amplitude and characteristics of the light detected back from the sensors. When no contact is made, an air layer may exist between the light source and the tissue that results in high air-tissue light reflections. These light reflections can cause detected signals for one of the sensors to be larger than expected while detected signals for the other sensors may be much lower than expected. Detected signals within a predetermined range may be indicative of appropriate contact between the probe and the tissue. An operator, for example, a physician or technician holding the probe in contact with the patient, may be alerted to an orientation of the probe where appropriate contact with the tissue is made.

Sufficient or insufficient contact between the imaging probe and the tissue surface can be communicated to the operator. For example, the probe 102 can include a light 116 or other visual indicator for visually alerting the operator to an adequate contact configuration. In another example, probe 102 can include a speaker 118 or other audible indicator for alerting the operator to an adequate contact configuration. The speaker 118 may emit a sound when the adequate contact configuration is reached. Alternatively, the speaker 118 may continuously emit sound, with the pitch or volume of the sound varying according to the condition of the contact between the imaging probe and the tissue surface. In another example, probe 102 can include a vibration mechanism or other mechanical indicator. When an adequate contact configuration is achieved, the probe 102 can vibrate to let the operator know. In still another example, the terminal 108 can provide an indication of the contact configuration, for example, by display on monitor 110. In further embodiments, the contact feedback may be used for feedback control of a positioning device or actuator that automatically moves the probe until a desired level of contact or contact pressure is established.

The imaging probe 102 includes a plurality of substantially monochromatic illumination sources (not shown) that can sequentially or simultaneously emit light into the patient body part 104. The illumination sources may be amplitude-modulated so as to allow discrimination of the detected signals. Each of the illumination sources can emit light at a different wavelength. Spaced from the illumination sources on a common interrogation face of the imaging probe 102 are a plurality of detectors (not shown), which are configured to detect the light that has been absorbed as it passes the patient. The number of illumination sources and detectors may be varied in different embodiments, and may number only one of each or dozens or more of each. In alternative embodiments, instead of monochromatic sources, the probe 102 may use one or more variable wavelength sources.

As noted above, the detected light may be processed to quantify the vasculature of the illuminated region, including the target region 106. The probe 102 processes signals from the detectors, for example, by demodulating the detected signals, to generate data indicative of the detected magnitude of light from each illumination source. The probe 102 may be configured to quantify absorbing and scattering components of the target region 106 as well morphological and chemical characteristics based on the extracted data, for example, scattering amplitudes and concentrations of oxy- and deoxy hemoglobin. Alternatively or additionally, the probe 102 may be configured to send reduced or raw data to a remote processor for further processing to determine generate data characterizing the target region 106. To transmit data, for example, the probe 102 may employ a wireless communication module, figuratively represented by an antenna symbol 112, that allows wireless transmission of information between the probe 102 and a wireless communication module, figuratively represented by the antenna symbol 114, connected to communication with the terminal 108.

Depending on the division of functions between the terminal 108 and probe 102, terminal 108 may be configured to perform further processing on data, initially generated from raw data, and relayed to it, by the probe 102. The raw intensity data measurements are voluminous and it transmitting over a communication channel would create a time bottleneck for end to end processing and/or require costly hardware or power expense. The probe may therefore advantageously be configured to perform initial processing and reduction of data for transmission by the host.

For example, terminal 108 may employ a multi-spectral evolution algorithm to quantify tumor vasculature based on detected light intensities. Terminal 108 may also include an input/output interface 110 for communicating details of the DOI investigation to a user. For example, the terminal 108 may provide an illustration of tumor vasculature or a comparison of quantities with prior obtained quantities so as to provide a visual assessment of treatment efficacy. The terminal 108 may also include tracking capability, for example, based on the wireless communication modules 112 and 114, so as to track the location of the imaging probe and thereby correlate an imaged location with a region of interest in the patient body part 104. Such information may be used to correlate the determined quantities with information obtained from other imaging modalities, such as, but not limited to, X-ray mammography, ultrasound, and MRI.

Figure 2:
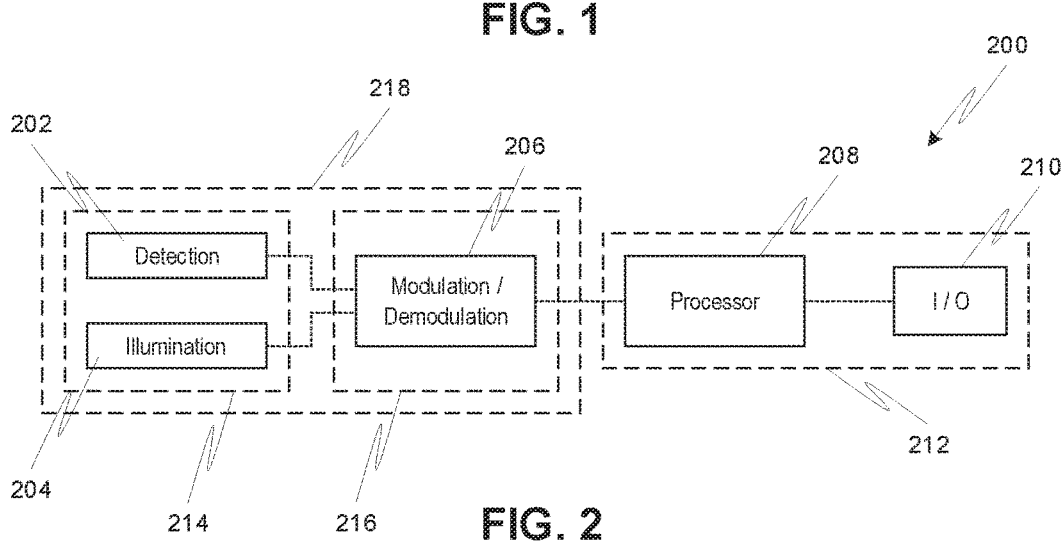
FIG. 2 shows components of an optical imaging system, according to one or more embodiments of the disclosed subject matter.

Referring to FIG. 2, a generalized schematic of an optical imaging system 200 is shown. The optical imaging system 200 can include an imaging probe portion 218 and a remote processing portion 212, which may be spatially and physically separate from each other. For example, imaging probe portion 218 can communicate with the processing portion 212 via a wireless communication link, for example, Bluetooth. Alternatively, imaging probe portion 218 may be connected to the processing portion 212 via a wired communication link, for example, an attached serial cable. Other connection schemes between the processing portion 212 and the imaging probe portion 218 are also possible according to one or more embodiments. For example, the imaging probe portion 218 may include a connector for interfacing with a respective receptacle on the processing portion 212 for periodically downloading data thereto.

The imaging probe portion 218 can include a probe head 214 and a probe body 216. The probe head 214 can include an illumination unit 204, which can have a plurality of individual light sources. The light sources can provide substantially monochromatic light and can be modulated to allow discrimination between the different light sources on detection. For example, the light sources are semiconductor-based light sources, such as laser diodes. The probe head 214 can also include a detection unit 202, which can have a plurality of individual detectors. The number of detectors can be greater or less than the number of light sources. For example, the ratio of light sources to detectors can be at least 2:1. The detectors can be arranged to detect light scattered and/or partially absorbed the object to be tested (e.g., a patient) when the imaging head is brought into contact with a surface thereof. For example, the detectors are semiconductor-based light detectors, such as silicon photodiodes.

The probe body 216 can include a modulation/demodulation unit 206 for control of the illumination unit 204 and the detection unit 202. The modulation/demodulation unit 206 can include a microcontroller, amplifiers, oscillators, counters, filters, laser diode drivers, analog-to-digital converters, receiver/transmitter interfaces, wireless communication modules, power supplies, or any other electrical circuit or component. For example, processor 206 can modulate the amplitude of light emitted by the individual light sources of the illumination unit 204 and can demodulate the signals detected by the detection unit 202. Modulation of the input light can be used to remove background and/or ambient light from the detected light signals.

The modulation/demodulation unit 206 can be configured to process the signals to determine desired tissue characteristics, for example, scattering amplitudes and concentrations of oxy- and deoxy hemoglobin by using a multi-spectral evolution algorithm. Alternatively, modulation/demodulation unit 206 may merely extract detected signal amplitude and send such data to processor 208 of remote processing portion 212. Processor 208 can be configured to further process and/or manipulate the data provided by the modulation/demodulation unit 206. For example, the processor 208 may be configured to determine desired tissue characteristics using a multi-spectral evolution algorithm. In still another alternative, raw data (e.g., without any demodulation processing) can be sent to the remote processor to perform the demodulation in addition to any additional processing.

Alternatively or additionally, processor 208 can compare newly obtained quantitative data with previously obtained quantitative data so as to provide an indication of treatment efficacy. Alternatively or additionally, processor 208 can combine the DOI data with data obtained by another imaging modality. For example, DOI obtained values for scattering amplitudes and concentrations of oxy- and deoxy hemoglobin can be combined or overlaid with an image of the interrogated region of the patient obtained via mammography. Input/output unit 210 can visually present the information to the system user and/or allow input from the user for instruction as to further processing.

Figure 4A:
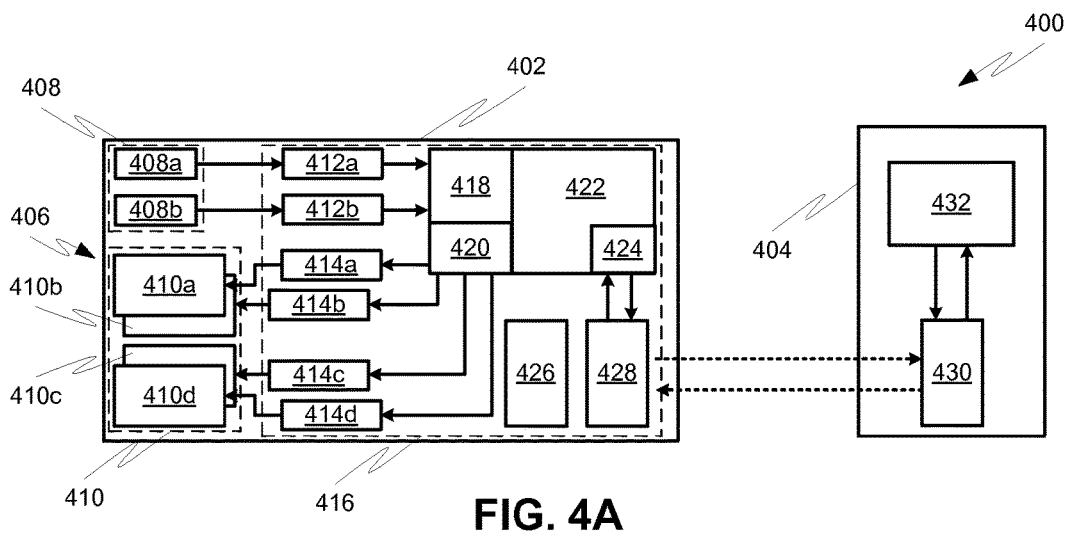
FIG. 4A shows components of a handheld imaging probe and a remote processor, according to one or more embodiments of the disclosed subject matter.
Figure 4B:
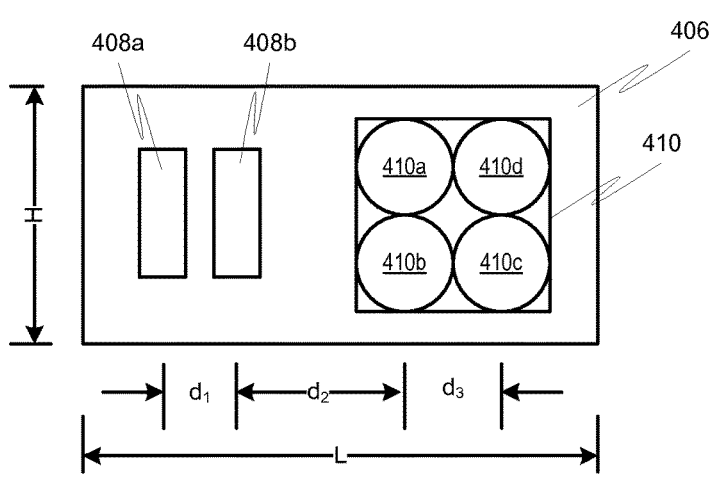
FIG. 4B shows the layout of detection and illumination components on an interrogation face of the handheld probe, according to one or more embodiments of the disclosed subject matter.

FIGS. 4A-4B show a layout of components of an optical imaging system 400. The imaging system 400 can include a handheld probe 402 that is self-contained such that no optical fibers, wires, or cables are needed to use the device. Conveying detector information to a user or remote terminal 404 can be performed using wireless (e.g., Bluetooth) communication, for example, wireless communication module 428 that communicates with a counterpart wireless communication module 430 of remote terminal 404. The probe 402 can resolve actual optical properties of scattering, oxy- and deoxy-hemoglobin using four source wavelengths and two detectors, for example, at a sampling rate of approximately 2.3 Hz.

The probe 402 can use radio-frequency modulated illumination to eliminate background light and reduce noise artifacts. The majority of the signal detection and demodulation can be performed in the digital domain, which allows for the wireless transmission of the final signal amplitude. A multispectral evolution algorithm can use the measured values to calculate absolute values for tissue-scattering, and concentrations of oxy- and deoxy-hemoglobin in tissue. The modulation of the input light provides several advantages including superior noise rejection (including ambient light) as well as the ability to illuminate the tissue simultaneously with multiple wavelengths. Alternatively, the probe can illuminate the tissue sequentially with individual wavelengths, for example, to allow use of a lower processing power microcontroller while running a lock-in detection algorithm and/or to allow for lower power consumption. However, more powerful microcontrollers can allow simultaneously illumination of the sample with all wavelengths, modulated at different frequencies, thereby improving the frame rate by a factor of 4 (e.g., to ~10 Hz).

The probe 402 can have an illumination unit 410 with four separate illumination sources 410a-410d that emit light at substantially a single wavelength. While not a requirement, each of the illumination sources can emit light at a different wavelength from the others. For example, a first illumination source 410a can emit light at a wavelength of 808 nm. A second illumination source 410b can emit light at a wavelength of 850 nm. A third illumination source 410c can emit light at a wavelength of 904 nm. A fourth illumination source 410d can emit light at a wavelength of 780 nm. Other wavelengths of light are also possible according to one or more contemplated embodiments. For example, four different wavelengths within the NIR wavelength range can be selected for the illumination sources so long as the separation between adjacent wavelengths is sufficient to allow discrimination in tissue properties and/or detection. For example, the separation between adjacent wavelengths selected for the illumination sources 410a-d can be at least 25 nm.

When the interrogation face 406 of the probe 402 is brought into contact with a surface of a sample to be imaged (e.g., the tissue surface), the illumination sources can emit light sequentially or simultaneously. For example, the input light from the illumination unit 410 can be generated by fours 5.6 mm-diameter laser diodes emitting light at wavelengths of 780 nm, 808 nm, 850 nm, and 904 nm. Alternatively, the light sources can emit light at wavelengths of 765 nm, 805 nm, 850 nm, 905 nm. The laser diodes can produce light having a power of between 1 mW and 10 mW, for example, less than 5 mW. The probe 402 may be equipped with a safety feature that only turns on the illumination sources when the probe is placed onto the sample The wavelengths for the illumination sources can be selected to provide a range of spectral information to reconstruct oxygenated hemoglobin (referred to herein as [$HbO_2$]), deoxygenated hemoglobin (referred to herein as [Hb]) and scattering. Each light source 410a-d can be driven by a respective light source driver 414a-d, for example, a 15 V laser diode driver. Drivers 414a-d can also include various electrical components to provide amplitude modulation of the individual wavelengths. For example, light source 410a-d can be amplitude modulated at a frequency ranging from 1 to 8 kHz, controllable by 20 kgΩ potentiometers. The modulation signal can be generated using a combination of a 1 kHz to 33 MHz oscillator, a binary counter and a low-pass filter. The power of each light source 410a-d can be controlled using a 20 kgΩ potentiometer that regulates the current to the respective drivers 414a-d. A general purpose input/output 420 of microcontroller 422 can be used to control the modulation of the individual light sources 410a-d.

The light passes through the sample and is absorbed/scattered as it travels to the detection unit 408, which is configured in reflectance geometry. The detection unit 408 can include at least two detectors 408a-b, for example, respective semiconductor photodetectors such as silicon photodiodes. The detectors 408a-b can be arranged at different distances with respect to each light source. Thus, a first detector 408a can be arranged farther from the illumination unit 410 than a second detector 408b. For example, the first detector 408a may be spaced from the second detector 408b by a distance of approximately 0.9 cm (i.e., $d_1$ in FIG. 4B), each light source 410a-d can be spaced from an adjacent one of the light sources by a distance of approximately 0.6 cm (i.e., $d_3$ in FIG. 4B), and a distance between the second detector 408b and the nearest light sources 410a, 410b can be approximately 1.8 cm (i.e., $d_2$ in FIG. 4B). In other examples, the second detector 408b may be located between 1.8 and 2.4 cm from the nearest light sources 410a, 410b (i.e., $d_2$) and the first detector 408a may be located between 2.7 and 3.3 cm from the nearest light sources 410a, 410b (i.e., $d_1+d_2$).

Respective electronics 412a-b can be provided for post detection processing of the signal obtained by each detector 408a-b. For example, detector electronics 412a-b can include a transimpedance amplifier. Each amplifier can have multiple gain settings. For example, the transimpedance amplifier can have gain settings of 10 kV/A, 100 kV/A, 1 MV/A, and 10 MV/A. For light source power between 1 and 5 mW, the second detector 408b (i.e., closer to the illumination unit 410) can use the 1 MV/A setting, while the first detector 408a (i.e., farther from the illumination unit 410) can use the 10 MV/A setting. These gain settings can utilize a bandwidth-extension technique.

Electronics 412a-b can also include appropriate filters for processing signals from the detectors 408a-b. For example, following the transimpedance amplifier, the signal can be high-pass filtered to remove any DC component of ambient or environmental light. The signal can also be passively low-pass filtered to prevent aliasing at the analog-to-digital converter 418. In addition, the signal may be further modified to optimize subsequent processing. For example, the signal can be offset to 1.5V to fully optimize the dynamic range of the input to the analog-to-digital converter 418.

The probe 402 can also include a microcontroller 422, which regulates operation of the illumination unit 410 and the detection unit 408 and processes the resulting signals. For example, microcontroller 422 can include a 12-bit analog-to-digital conversion circuitry. The analog-to-digital converter logic can be configured to sample at 75 kHz and to acquire 150 samples for each measurement. Upon acquisition, the microcontroller 422 can perform digital lock-in detection to extract the amplitude from the detected sinusoidal signal from detection unit 408. This algorithm can use averaging filters combined with modulation and sampling constraints to digitally extract the amplitude and/or phase while reducing noise.

The demodulated amplitude can then be conveyed to a wireless communication module 428 via a universal asynchronous receiver/transmitter interface 424. For example, the wireless module 428 can be a Bluetooth module with a relatively small form factor (for example, on the order of 13.4 mm×25.8 mm×2.0 mm) and with relatively low power consumption (for example, less than 100 mA @ 3 V). The Bluetooth module can also provide secure communication with 128 bit encryption, error correction for guaranteed packet transfer, and a Class 1 antenna that provides up to 100 m of wireless range.

The wireless module 428 transmits the measurements to a host or terminal 404 via a counterpart wireless module 430 contained therein. For example, a Bluetooth-capable computer can pair with the Bluetooth module of the probe 402 (e.g., by providing the correct pairing code) and thus communicate via a virtual serial communication port to a user interface. The remote terminal 404 can include a processor 432 for performing subsequent manipulation of the measurement data and/or for allowing user input, for example, via a graphical user interface. For example, the remote terminal 404 can be a personal computer, tabular computer, cellular phone, smartphone, server, or any other computing or processing device.

Probe 402 can include an on-board power supply 426, such as a battery or other power storage mechanism. The power supply may be configured to provide at least 120 mA at 3 V. A low-dropout voltage regulator (not shown) can be provided in probe 402 to take any input voltage between 3 and 12 V and convert it to 3 V. For example, power for the probe 402 can be provided by a 9 V D-type battery.

With no incident light on the detectors the dark noise of the probe can be on order of 160 µV. The maximum possible input value can be on the order of 3 V peak-to-peak, thereby giving the probe a dynamic range of 85 dB for the single 10 MV/A gain setting. From measurements made on a tissue-like optical phantom, the signal-to-noise ratio (SNR) of the wavelengths can be between 36 dB and 51 dB, which range may results from the differences in absorption at the various wavelengths.

When using a lower powered processor and sequential illumination, probe speed may be limited by the time required to demodulate the acquired signal. For example, it may take approximately 2 ms to acquire 150 samples followed by 52 ms to demodulate the data and send it to the wireless communication module. This 54 ms acquisition time is repeated for each of the four wavelengths and each of the detectors, ultimately giving a sampling speed of 2.3 Hz. It takes the laser diodes approximately 5 ms to settle following switching. This settling time can be coordinated to take place during the time that the microcontroller is demodulating the data from the previous wavelength. A summary of the probe's parameters and performance is shown in Table 1.

TABLE 1

Summary of the wireless handheld probe parameters and performance.

| Parameter | Value |
| --- | --- |
| Wavelengths (4) | 780 nm, 805 nm, 850 nm, 904 nm |
| Detectors | 2 |
| Mode | Continuous Wave (CW) |
| Frame Rate | 2.3 Hz |
| Dynamic Range | 85 dB |
| Dark Noise | 160 µV |
| SNR | ~50 dB |
| Power Consumption | 120 mA @ 3 V |
| Size | 11.5 × 16 × 2.5 cm |

Figures 3A, 3B:
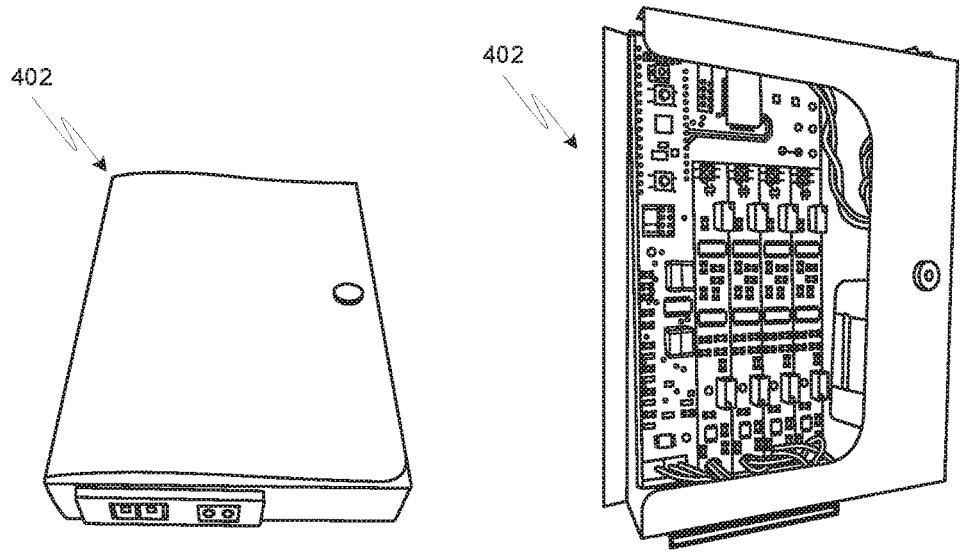
FIGS. 3A-3B are images of a handheld imaging probe, according to one or more embodiments of the disclosed subject matter.

The arrangement of the detection unit 408 and the illumination unit 410 as well as the overall packaging can provide for an easily handheld device. For example, the probe 402 can be defined by a case (e.g., plastic) that has an interrogation face with dimensions of approximately 6 cm (i.e., L in FIG. 4B) by 2 cm (i.e., H in FIG. 4B). Overall probe dimensions can be, for example, 11.5 cm×16 cm×2.5 cm. Such a construction allows the probe 402 to be held easily while bringing the probe into contact with a variety of tissue surfaces. A photograph of the probe 402 is shown in FIG. 3A. FIG. 3B shows the probe 402 with the enclosure opened to partially expose the inner electronics.

As referenced above, a diffuse reflectance spectroscopic techniques can be used to derive the optical properties of scattering, [Hb], and [HbO$_2$] in tissue. The diffuse spectroscopic technique is based on the reflectance measured at multiple locations on the surface of the sample, where the diffuse reflectance depends solely on the absorption coefficient $\mu_a$ and the reduced scattering coefficient $\mu_s'$ and the source-detector separation d. Assuming a semi-infinite homogeneous medium, the closed-form analytic solution for the spatially resolved reflectance is given by:

$$R(d)_{dc} = \frac{1}{4\pi\mu_t'}\left[\left(\mu_{eff} + \frac{1}{r_1^2}\right)\frac{\exp(-\mu_{eff} r_1)}{r_1^2} + \left(\frac{4}{3}A + 1\right)\left(\mu_{eff} + \frac{1}{r_2}\right)\frac{\exp(-\mu_{eff} r_2)}{r_2^2}\right], \quad (1)$$

where $$r_1 = \sqrt{\left(\frac{1}{\mu_t'}\right)^2 + d^2}, \text{ and } r_2 = \sqrt{\left(\frac{\frac{3}{4}A + 1}{\mu_t'}\right)^2 + d^2}. \quad (2)$$

Here $\mu_{eff}$ is the effective attenuation coefficient ($\mu_{eff} = \sqrt{3\mu_a\mu_s'}$), $\mu_t'$ is the total transport coefficient ($\mu_t' = \mu_a + \mu_s'$), A is the internal reflection parameter that takes into account the refractive index mismatch at air-tissue interface. To find $\mu_a$ and $\mu_s'$, a slope based approach can be used wherein the analytic solution (Eqn. 1) is fit to the measured values of R(d), which makes use of the linear correlation between R(d) and d. In other words, a plot of log(d$^2$R(d)) versus d can be used to estimate $\mu_{eff}$. To separate $\mu_a$ and $\mu_s'$, one of the following can be used: the absolute overall diffuse reflectance over the entire surface, the reflectance at small d to obtain $\mu_s'$, the intercept of d$^2$R(d) versus d to estimate $\mu_s'$, and time-resolved techniques to assume Once $\mu_a$ and $\mu_s'$ are obtained at multiple wavelengths, the results can be combined to obtain [HbO$_2$] and [Hb]. However, the slope-based approach can be sensitive to noise, since small errors in the measurement can lead to a large error in the slope obtained through a least squares fitting procedure. To reduce this error, the amount of data can be increased, for example, by increasing the number of detectors, which in turn leads to an increase in the size of the probe. Such a solution may detract from the desired handheld nature of the device.

To overcome these difficulties with the slope-based approach, a multi-spectral direct method can be employed.

The multi-spectral direct method can use data from all wavelengths simultaneously to estimate optical properties. The multi-spectral direct method exploits the following linear correlation between the tissue absorption and the tissue chromophore as:

$$\mu_a(\lambda) = \sum_{i=1}^{N_c} \varepsilon_i(\lambda) C_i, \text{ and } \mu_s' = A\lambda^{-b}, \quad (3)$$

where $\varepsilon_i(\lambda)$ and $C_i$ are the absorption extinction coefficient and the concentration of the ith chromophore in tissue. $N_c$ is the number of tissue chromophores that contribute to the absorption at wavelength $\lambda$. The scattering parameters A and b are the scattering amplitude and the scattering power, respectively. The multi-spectral direct method reconstructs $C_i$, A, and b directly instead of retrieving $\mu_a$ and $\mu_s'$ independently for each wavelength and decomposing the results as done in a two-step method. The direct approach enables the use of all wavelength data simultaneously to recover the parameters $C_i$, A, and b, which are wavelength independent, thereby improving upon the non-uniqueness problem of diffuse optical imaging.

These benefits can be used for spatially resolved spectroscopy where bulk optical properties are to be obtained for semi-infinite medium. The spatially resolve spectroscopy problem with the direct approach can be formulated as the following inverse problem, where the optimal solution can be found by minimizing the misfit between predictions $R_d$ and measurements $z_d$ of the reflectance on the tissue surface. In particular, $$F(x) = \sum_{\lambda,d} (R_d^\lambda - z_d^\lambda)^2, \quad (4)$$

where x is the vector of all unknowns, e.g., $x=(C_j, A, b)$. Nonlinear least-squares methods may be used to solve Eqn. 4. However, gradient-based search methods may be sensitive to random noise and may fail to find the global least-squared minimum. To avoid such a problem, a global-search multi-spectral spatially resolved spectroscopy algorithm based on a genetic algorithm (e.g., evolution strategies), which do not require calculation of a noise-sensitive gradient, can be used to reliably find the global minimum of Eqn. 4. Evolution strategies (ES) are algorithms that imitate the principles of evolution and heredity in nature for inverse problems in engineering applications.

Figure 5:
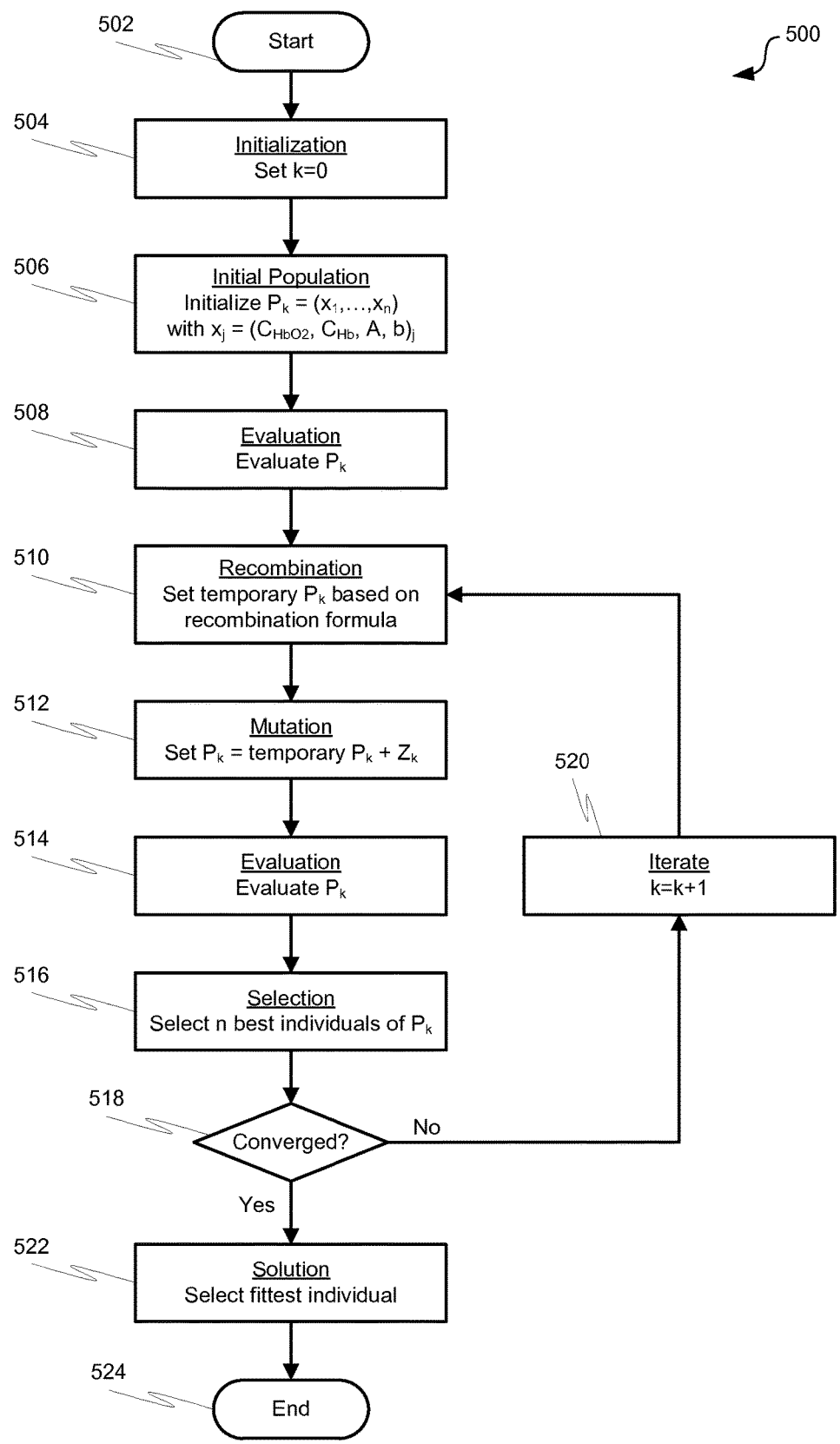
FIG. 5 is a process flow diagram of an evolution strategy algorithm, according to one or more embodiments of the disclosed subject matter.

The general structure of the ES algorithm 500 as used herein is described with respect to FIG. 5. At 502, the process begins and proceeds to 504 for initialization. At 504, the iteration parameter k is set to zero. Proceeding to 506, an initial population $P_k$ of individuals is set. In particular, the population $P_k=(x_1, \ldots, x_n)_k$ at iteration k includes a number of individuals where each individual $x_j$ represents a potential solution to the inverse problem under investigation. At 508, each individual $x_j$ is evaluated using the objective function (Eqn. 4). The process then proceeds to 510.

At 510, individuals are randomly recombined. A temporary population vector $\tilde{P}_k=(\tilde{x}_1, \ldots, \tilde{x}_m)$ is first built through the recombination process. The recombination can be performed according to:

$$\tilde{x}_j^i = \tfrac{1}{2}(x_{a,j}^i + x_{b,j}^i), \quad (5)$$

where $\tilde{x}_j^i$ denotes the i-th component of the j-th temporary individual vector and $x_{a,j}^i$ and $x_{b,j}^i$ are the i-th components of two individuals randomly chosen from the population vector.

At 512, using the above noted temporary population vector $\tilde{P}_k$, the next m individuals (m>n) are created by the following mutation process:

$$x_j^{mut} = \tilde{x}_j + \sigma_j' \cdot N_j(0,1), \text{ where } \sigma_j' = \sigma_j \exp(\tau' N_j(0,1) + \tau N_j(0,1)), \quad (6)$$

where $\sigma_j$ is a mutation step size for the update of the j-th individual (for example, set to be 0.0001 multiplied by some typical value of each unknown parameter), $N(0,1)$ denotes the normally distributed random variable sampled only once during the k-th iteration, and $N_j(0,1)$ denotes the normally distributed random variable sampled anew for each j-th individual. The proportionality factors $\tau$ and $\tau'$ can be set as $\tau \propto 1/(2n)^{1/2}$ and $\tau' \propto 1/(2n^{1/2})^{1/2}$.

At 514, each of the mutated individuals $x_j$ is evaluated using the objective function (Eqn. 4), and the n fittest individuals are selected to generate the new population $P_{k+1}=(x_1, \ldots, x_n)_{k+1}$ at 516. At 518, the individuals are evaluated to determine if there is sufficient convergence to a solution or if some other criteria indicating termination of the iterative process has been meant (e.g., where k is equal to or exceeds a predetermined maximum number of iterations). If sufficient convergence has not been achieved, the process proceeds to 520 where k is incremented and the recombination/mutation (i.e., 510-516) is repeated. Otherwise, the process proceeds to 522 where the fittest individual is selected. The process thus terminated at 524.

The ES algorithm described herein was evaluated through numerical experiments. For the scattering parameters, it may be sufficient to focus on the reconstruction of the scattering amplitude A alone since there exists strong crosstalk between A and b, and four wavelengths of data (available from the wireless probe) may not necessarily be sufficient to reliably reconstruct both A and the scattering power b. To this end, synthetic data corrupted by noise level of 15 dB were generated using the analytic solution (Eqn. 1) for semi-infinite approximation for a number of cases with different optical properties which vary from 20 μM to 100 μM for [HbO$_2$] and [Hb] and from 7000 to 8000 $10^{-6b}$ mm$^{b-1}$ for A with a fixed b of 1.34 (e.g., a typical value for Intralipid® and/or bulk breast tissue) scatterers.

FIGS. 6A-6C show reconstructed [HbO$_2$], [Hb] and A versus their respective true values in a numerical phantom. The results show that for the above described conditions the ES algorithm can retrieve the actual values of absorption and scattering parameters with reasonable accuracy, although the scattering coefficients may be slightly underestimated due to the lower sensitivity of continuous wave data as compared to frequency domain data. While continuous wave instrumentation allows for lower cost with faster measurements, it may be sensitive to inter-parameter crosstalk and may have difficulty accurately separating absorption and scattering.

Experimental studies on an optical phantom were performed to validate the handheld probe. Using a series of liquid phantoms, the relationship between the expected values of absorption, scattering, and chromophore concentration and the reconstructed values can be explored. To reconstruct the absolute values of absorption and scattering parameters in the medium, the target measurement data was normalized to a reference medium with known optical properties. Measurements were made at the surface of a cubic box (8 cm on a side) filled with 500 ml of thirty different solutions. Each solution included an aqueous mixture made up of Intralipid® (e.g., 20% fat emulsion), black ink, and near-infrared dye. Intralipid® has well-documented optical properties and has been used in phantom studies to mimic tissue optical properties. Black ink is also used in optical phantoms and is a water-soluble absorber that has a flat absorption spectrum in the probe wavelength range. The near-infrared dye was water soluble with a peak absorption at 970 nm and therefore displayed a spectral response different from the blank ink in the near-infrared range. The ranges for $\mu_a$ and $\mu_s'$ were selected based on the typical optical properties of breast tissue.

In a first experiment, a reference solution of 3.2 by volume (32 ml/l) of Intralipid® (20%) was used with no added ink or dye. This provided a medium where the absorption is predominantly due to water, which results in higher absorption at higher wavelengths (expected $\mu_a$ of 0.023, 0.019, 0.042, and 0.068 cm$^{-1}$ at 780 nm, 808 nm, 850 nm, and 904 nm, respectively). The scattering in the medium can be due to the Intralipid® scatterers and decreases at higher wavelengths (expected $\mu_s'$ of 6.74, 6.48, 6.12, and 5.7 cm$^{-1}$ at 780 nm, 808 nm, 850 nm, and 904 nm, respectively). The reduced scattering coefficient can be increased by increasing the concentration of Intralipid® from 3.4% (34 ml/l) to 5.2% (52 ml/l) in increments of 0.2% (2 ml/l), thereby resulting in a $\mu_s'$ ranging from approximately 6 to 10 cm$^{-1}$. An increase in the Intralipid® concentration does not necessarily change the absorption of the solution.

FIG. 7A shows both the theoretical (solid and dashed lines) and the experimentally derived values (markers) for $\mu_a$ for varying concentrations of Intralipid®. As expected, $\mu_a$ shows no dependence on Intralipid® concentration, and the calculated values for absorption closely match the expected values for water. Conversely, FIG. 7B shows that $\mu_s'$ increases linearly with increasing Intralipid® concentration due to the increased concentration of scatters. The setup may underestimate the reduced scattering (e.g., have an average relative error on the order of 6%).

For the second experiment, a reference solution of 4.8% (48 ml/l) Intralipid® and 0.024 ml/l of ink dilution were used. In this experiment, absorption is due to both water and ink (expected $\mu_a$ of 0.042, 0.038, 0.060, and 0.086 cm$^{-1}$ at 780 nm, 808 nm, 850 nm, and 904 nm, respectively) while scattering is due to Intralipid® (expected $\mu_s'$ of 9.84, 9.46, 8.93, and 8.31 cm$^{-1}$ at 780 nm, 808 nm, 850 nm, and 904 nm, respectively). The absorption coefficient can be increased by increasing the ink concentration by 0.024 ml/l per step from 0.048 ml/l to 0.24 ml/l, which resulted in an increase in $\mu_a$ of approximately 0.0192 cm$^{-1}$ per step. However, increasing the ink concentration does not affect the scattering properties of the medium.

FIGS. 8A-8B show the results of the second experiment, where the theoretical values for absorption and scattering are shown by solid and dashed lines, and experimentally derived values are shown by markers. In FIG. 8A, $\mu_a$ has a linear relationship to the ink concentration with an average relative error of 3%. The increased ink concentration does not affect the scattering of the solution, as shown in FIG. 8B. Rather, $\mu_s'$ remains relatively constant for the various concentrations of ink. Similar to the first experiment, the scattering is underestimated by approximately 7% on average, an effect which may be accentuated at longer wavelengths.

In order to explore the probe's ability to accurately separate two chromophores, such as oxy- and deoxy-hemoglobin, measurements were performed on a series of liquid optical phantoms with varying amount of ink and dye (e.g., Black India ink and Epolight 2735, 0.05 g in 50 ml DI water). In each experiment, a low and high absorbing solution was used to calibrate the probe. First, solutions of 4% Intralipid® (40 ml/l), 0.05 ml/l of dye, and 1.5 ml/l to 3.5 ml/l of ink (in steps of 0.5 ml/l as phantoms 1-5) were measured. The expected and measured values of the ink and dye volumes are shown in FIG. 9A. Second, a solution of 4% Intralipid® (40 ml/l), 1 ml/l of 1% ink dilution, and 1 ml/l to 3 ml/l of dye (in steps of 0.5 ml/l as phantoms 6-10) were measured. The expected and measured values of the ink and dye volumes are shown in FIG. 9B. As reflected in FIGS. 9A-9B, increasing the ink or dye concentration does not affect the scattering properties of the medium.

Figure 10A:
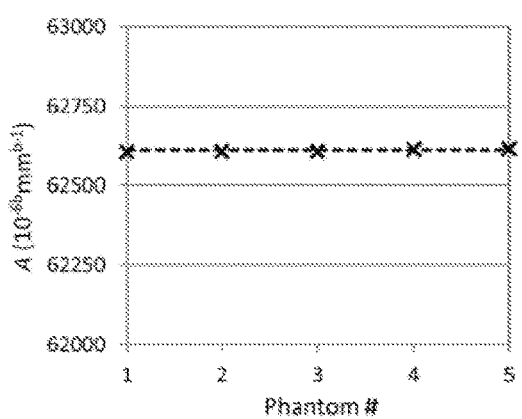
FIGS. 10A-10B are graphs of reconstructed values for scattering A for linearly increasing amounts of ink and linearly increasing amounts of dye, respectively, where dashed lines represent the actual value and the 'X' marker represents measured values.
Figure 10B:
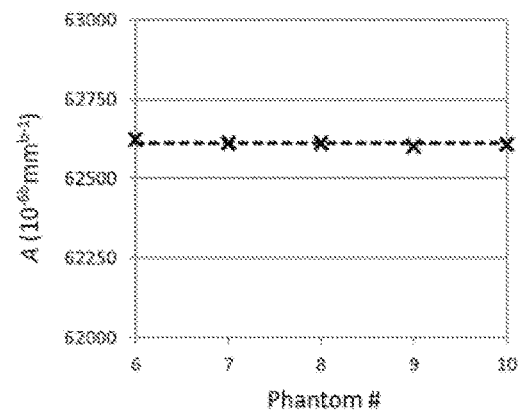

The expected and measured values for the scattering parameter A for the experiments of increasing ink and increasing dye concentrations are shown in FIGS. 10A-10B, respectively. The results disclosed herein demonstrate that the probe can distinguish between two different optically absorbing chromophores. The relatively small error in deriving the precise ink and dye volumes may be due to the fact that the wavelengths employed by the probe were optimized for differentiating oxy- and deoxy-hemoglobin as opposed to differentiating the spectra of the ink and the dye.

In embodiments of the disclosed subject matter, a handheld wireless probe can be used for diffuse optical tissue spectroscopy. The probe can be created using relatively low-cost components and thereby presents an inexpensive, portable, and user-friendly device for clinical optical measurements. By using at least four interrogation wavelengths and at least two detector positions, the probe can accurately resolve absolute measurements of absorption and scattering using a multi-spectral evolutionary reconstruction algorithm. However, other reconstruction algorithms to solve for absolute measurements of absorption and scattering are also possible according to one or more contemplated embodiments.

In embodiments of the disclosed subject matter, the imaging probe can have an interrogation face designed to accommodate various surface topographies and geometries encountered in profiling a patient. For example, the interrogation face may be formed of a sufficiently flexible material so as to conform to the patient or tissue surface when placed in contact therewith. For example, the interrogation face may include an optically transparent (or at least translucent) liquid, gel, or air-filled bladder that provides a conforming mechanical interface to the body surface. For example, the interrogation face can include an optical coupling with similar scattering and/or absorption properties as the tissue being imaged. The bladder may transmit light between the interrogation face and the body in a predictable manner owing to the known properties of the bladder interior. The bladder may have an optically transparent or translucent casing and may be permanently sealed. A kit of bladders having different shapes may be provided, each being configured for releasable attachment to the interrogation face. The flexibility of the casing may allow for smooth and gentle movement over a body contour. Also, the initial shape of a bladder may provide for partial insertion into recessed anatomical features such as an armpit, ear canal, nasal passage, or the region of the eye. In embodiments, the interrogation face may be adapted to attach to one or more interrogation components that are interchangeable as discussed infra with reference to FIGS. 12A, 13A, and 14A.

Alternatively or additionally, the imaging probe can be provided with a plurality of interchangeable probe heads for use in interrogating different anatomical features or tissues. For example, FIGS. 11A-11B show an imaging probe 1002 that includes a probe head 1004 and a probe body 1006. The probe head 1004 can include a detection unit 1008 with a plurality of detectors and an illumination unit 1010 with a plurality of light sources. The detectors and light sources can be arranged on an interrogation face 1022 of the probe head 1004. Probe body 1006 can include processing electronics 1012, for example, for controlling the illumination unit 1010 and/or processing signals from the detection unit 1008. The processing electronics 1012 may communicate with the illumination unit 1010 and the detection unit 1008 via one or more electrical connections 1016 passing through the probe body 1006 and interfacing with respective electrical connections 1012 in the probe head 1004. The probe head 1004 may be detached from the probe body 1006 at interface 1014, where a probe head connector 1018 can fit with a counterpart receptacle 1020 on the probe body 1006.

Once the probe head 1004 is detached, the probe body 1006 can be fitted with one of a plurality of different probe heads, as illustrated in FIGS. 12A-14B. Each of the probe heads of FIGS. 12-14 can have a different configuration designed to accommodate different anatomical features and/or provide different source/detector configurations. For example, the probe head of FIGS. 12A-12B can have a substantially concave interrogation surface 1022. In contrast, the probe head of FIGS. 14A-14B has a substantially convex interrogation surface 1022. Other shapes and configurations for the interrogation surface 1022 are also possible according to one or more contemplated embodiments. For example, the interrogation surface 1022 may have a wave or undulating configuration.

The probe head 1004 may include a unique identifier or an identifier of a class of product to which it belongs that allows the probe body 1006 or an attached host to acquire information about the configuration of the probe head 1004. For example, the probe head 1004 may carry a data carrier such as an RFID tag, a smart chip, a bar code or a mechanical code that indicates the features of the probe head. Different probe heads can have different mechanical interfaces but they can also have different numbers of sources and detectors or different arrangements or spacing thereof. They can also provide different directly addressable features such as the frequencies of light they can be programmed to generate and detect or other functional aspects.

Alternatively or additionally, the probe head can have a substantially planar surface but a different arrangement of illumination sources and detectors, as shown in FIGS. 13A-13B. For example, detector 1008a can be located on an opposite side of the illumination unit 1010 from the other detector 1008b. Alternatively or additionally, the individual light sources 1010a-d of the illumination unit 1010 can be arranged in a different configuration than a two-by-two array. Other arrangements for the detectors and/or light sources, number of detectors, and number of light sources are also possible according to one or more contemplated embodiments.

The size of the device can be suited for hand-held operation. Although specific dimensions for the size of the device have been disclosed herein, embodiments of the disclosed subject matter are not limited thereto. Rather, the size of the device can be further reduced by appropriate design and selection of device components, for example, by selecting components with smaller footprints, a smaller internal power source, and/or increasing the density of components in the device. In addition, the probe head can be made to have a different size and shape than the probe body. For example, the probe body may be sized and shaped to allow one-handed control while the probe head is sized and shaped for imaging a particular anatomical structure. A plurality of different sized and/or shaped probe heads may be provided in a imaging probe kit to allow appropriate selection of a probe head geometry for imaging a desired tissue or feature with the same probe body. The probe body can include buttons, switches, or other interfaces on its surface to allow actuation of the various features of the imaging probe by the hand holding the imaging probe during use.

Furthermore, while specific imaging frequencies have been disclosed herein (e.g., 2.3 Hz), other imaging frequencies are also possible according to one or more contemplated embodiments. For example, the imaging speed may be increased by selecting a more powerful microcontroller and/or using simultaneous illumination by multiple wavelengths. Moreover, while specific interrogation wavelengths have been discussed herein, embodiments of the disclosed subject matter are not limited to these specific examples. Rather, the wavelengths can be selected based on the tissues, materials, chemicals, and/or chromophores desired to be investigated in a particular application. For example, wavelengths can be selected to correspond to melanin, fat, collagen, water, oxy- and deoxy hemoglobin, scattering materials, or any other chemical or material that is most relevant for a particular application.

The disclosed device and algorithm can facilitate future clinical studies exploring the optical signatures of tumor regions in the breast. However, applications of the disclosed systems, device, methods and/or algorithms are not limited to breast imaging. Indeed, embodiments of the disclosed subject matter can provide a fast and easy way to make static and dynamic measurements on many other tissues, such as, but not limited to, brain, limbs, and breast, without the need for specific interfaces for each application. For example, the system could also be used for finger imaging for arthritis detection and brain imaging as well as for studying peripheral arterial disease (PAD). The ease of use, portability, and low cost of this device will complement many existing clinical optical studies by providing real-time measurements and may create opportunities for new clinical applications.

Referring now to FIGS. 15A through 15D, an imaging probe kit 1003 includes a set of probe heads 1004A, 1004A, and 1004C each of which attaches to the probe body 1006. Each probe head 1004A-1004C can include a detection unit as described above with a plurality of detectors and an illumination unit with a plurality of light sources also as described above. The detectors and light sources are arranged on a respective interrogation faces 1022A, 1022B, and 1022C of the probe heads 1004A, 1004B, and 1004C, respectively. As in the previous embodiment, probe body 1006 can include processing electronics 1012, for example, for controlling the illumination unit and/or processing signals from the detection unit. The processing electronics 1012 may interface electrically with at attached one of the probe heads 1004A through 1004C. The probe head may be selected based on a particular target body part to be interrogated, taking advantage of the particular characteristics of the probe head 1004A, 1004B, or 1004C. Simple examples of probe heads are shown, but any kind of variation may be provided with variously shaped interrogation faces 1022A through 1022C. In addition, the kit 1003 may include respective sets of interface adapters, for example for probe head 1004A, interface adapters 1020A, 1020B, and 1020C may take the form of variously shaped bladders of clear or translucent fluid or rigid or flexible members of uniform composition that transmit light. For example, the adapters may be bladders filled with lipid or other fluid with appropriate interface characteristics. For another example, they may be rigid or somewhat flexible articles of uniform composition such as thermoplastic with optical coating.

The kit 1003 may include respective sets of interface adapters, for example for probe head 1004B, interface adapters 1020D and 1020G may also take the form of variously shaped bladders of clear or translucent fluid and for probe head 1004C, interface adapters 1020E and 1020F may also take the form of variously shaped bladders of clear or translucent fluid. The adapters 1020A through 1020G may be flexible walled with adhesive or smooth faces that cling to a respective interrogation face 1022A, 1022B, or 1022C.

The adapters may have various characteristics such as differently shaped faces, thicknesses of the shell material at the face, and different amounts fluid. A highly flexible and/or elastic face 1021G may be useful for application to lump surfaces, for example. A narrow and relatively rigid adapter 1020B may present a face that is only slightly flexible. In use, an adapter like 1020G may allow the taking of OT measurements over a complex shape surface such as the face of a closed eye, permitting the taking of measurements through a closed eyelid or the top of a foot or side of an ankle. Adapters may be particularly useful for unpredictable anatomy such as the site of a contusion where swelling has distorted the surface.

FIG. 15E illustrates an imaging probe head 1044, which may be included in a kit and attached to probe body such as 1006. The probe head 1044 has a longitudinal interrogation member 1043 with a rounded face 1045 with detectors and light sources distributed over it. As in the previous embodiments, a variety of adapters may be provided such as indicated at 1046A, 1046B, and 1046C, each with a respectively shaped face 1047A, 1047B and 1047C. The adapters may be slipped over the interrogation member 1043. FIG. 15F shows an adapter 1032 that may be clipped to a probe head 1036. The adapter 1032 is carried by and part of a chassis portion 1030 with attachments adapted for interference attachment to the probe head 1036 such as to press an adjacent face 1034 against an interrogation face 1035 of the probe head 1036.

FIGS. 16A and 16B shows respective light guide adapters 1102 and 1134 that guide light to and from detectors and sources 1110, 1108, 1110, and 1138, respectively such that the effective distance between the possible source/detector pairs of a probe 1104 can be varied by attachment of a selected adapter such as 1102 or 1134. Thus light emitted through the end of a light guide 1131 may be applied to body surface as if the probe head were shaped correspondingly and the position of the source 1110 were placed at that position and on the illustrated interrogation surface 1133. Note that the spacing between the ends of the light guides 1106 ends 1101 and 1103 may be different from the spacing of the sources and detectors 1110 and 1108. The spacing may be expanded or reduced in respective embodiments. The number of points where light is received may be reduced from the native number of the imaging probe head as well. Software that controls the activation of sources and detectors 1110 and 1108 may be adapted by the engagement of an adapter, either automatically by a machine readable identifier on the adapter (for example an RFID, a bar code, or encoded chip) or by means of user-entered identification information.

FIG. 17A shows an adapter 1133 configured to apply and receive light signals in a transmission mode by guiding light from a source 1108 to a light guide 1137 whose end opposes the end of a light guide 1131 that guides received light to a detector 1110. Flexible adapters 1139 such as lipid filled bladders may be included. A kit with differently sized adapters 1139 may be provided with adapter 1133 along with the foregoing adapter kits according to any of the described embodiments. Another mechanism for providing transmission mode capability is illustrated in FIG. 17B in which a support 1140 attaches probe heads 1104 so that they face each other with opposing sources and detectors 1108 and 1110. A flexible conforming adapter 1142 may also be provided. A kit may include multiple probe heads to allow for varying configurations such as this. The support may integrate light guides 1144. A slot defined in either of the adapters 1133 and 1140 may permit the insertion of a body part, such as a body extremity. Slots defining more open angles may provide partly transmission mode and partly reflection mode capability. Although in the foregoing imaging devices and their features were illustrated using embodiments with sources and detectors that are spaced apart in a single axis, it is possible, as illustrated by a couple of examples in FIGS. 18A and 18B to arrange them along multiple axes. For example, probes 1250 and 1260 show sources 1252 and detectors 1254 arranged along multiple axes.

Figure 19A:
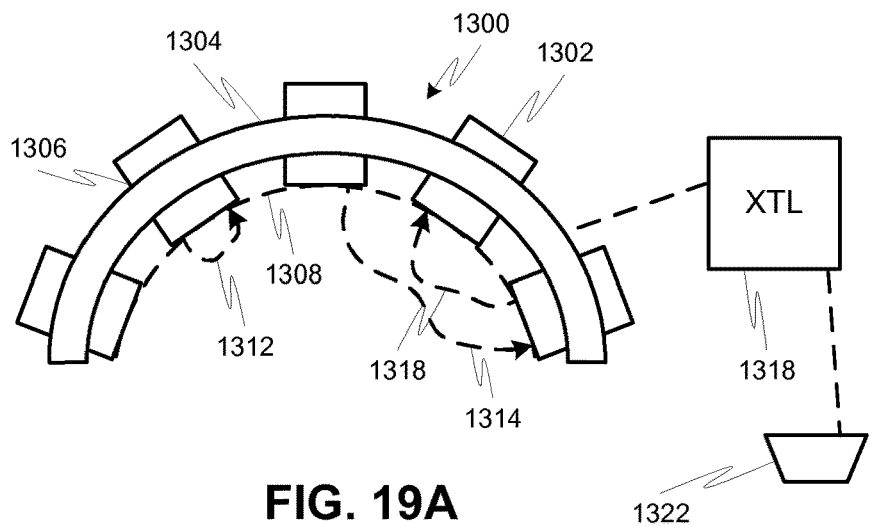
FIG. 19A shows a rigid support with receptacles that can receive optical tomography imaging probes, which may be wireless, wired, or light-guide attached probes, and position them for combined use for interrogating a predefined body part.

FIG. 19A shows an embodiment of an optical tomography probe configuration 1300 which is made up of modular units based on the wireless probe embodiments described herein. A rigid support 1304 contains receiving portions 1306 into which wireless or wired (or light-guide connected) optical tomographic probes may be attached. The receiving portions 1306 may be configured such that they position and orient probe units 1302 in predefined locations and orientations by means of the mechanical configuration of the support 1304. Each probe unit may be self-identifying to a connected control unit 1318. The support may have electrical as well as mechanical connectors as part of the interface to permit a controller 1318 to determine the positions of the respective probe units 1302 such that it can address each one respectively for control and data acquisition. By combining multiple probe units with a common basis of control, transmission mode interrogation using a source in one probe unit and a detector in another unit (as indicated at 1314 and 1318) may be defined. At the same time, any of the units may also be operated for reflectance mode operation in addition or alternatively as indicated by the figurative light path identified by reference numeral 1312. In an embodiment, each probe unit has a chip or other data carrier such as a mechanical encoded identifier, a bar code, an RFID tag, etc.) containing a unique identifier and the support or controller has a data capture device to convey the identity to a data store used by the controller. The data store may be local or remote. Additional data about the capabilities of each unit 1302 may also be accessed either provided by the data carrier directly or derived based on the unique identifier, for example, by the controller accessing a server that correlates additional information about the units with the unique identifier. The capability data may indicate the characteristics of the units such as output power, positions and frequencies of sources and detectors, and other information that may allow the controller 1318 to coordinate the operation of the units 1302 for performing an interrogation of the target tissue 1308.

In a system, multiple different supports 1304 with varying shape and size may be provided for the inspection of different body parts and sizes of body parts such as limbs, heads, breasts, etc. The disclosed embodiments may provide similar capability to optical tomographic systems that are specially configured for a particular application, but provide much more flexibility and evident economies. Further flexibility may be provided by adapter embodiments such as described with reference to FIGS. 11A through 17B. The adapters, for example flexible embodiments, may be useful for fine-tuning the mechanical adjustment to the body part being inspected. For example, the adapters may be selected to bridge a small between a corresponding probe unit and the surface of the body part 1308. The adapters 1322 may be also be provided with identifiers (e.g., data carriers as described with reference to the probe units or similar) at least to indicate the size and shape of the adapter to permit the controller 1318 to convey this information to a host for processing the images as described herein. In addition, the controller or host may be configured to generate a diagnostic log that includes the configuration used for interrogating the tissue including the identifiers of the probe units and adapters used. These data may be bundled with the tissue image data or reduced from the image data and incorporated in a diagnostic log. These data may be accessed for following up a patient, to produce time series information for following the progression of a disease or treatment. For example, the configuration data may allow a technician to recreate the particular configuration used for an earlier inspection, thereby making image data acquired therewith more suitable for direct comparison an earlier acquisition.

Figure 19B:
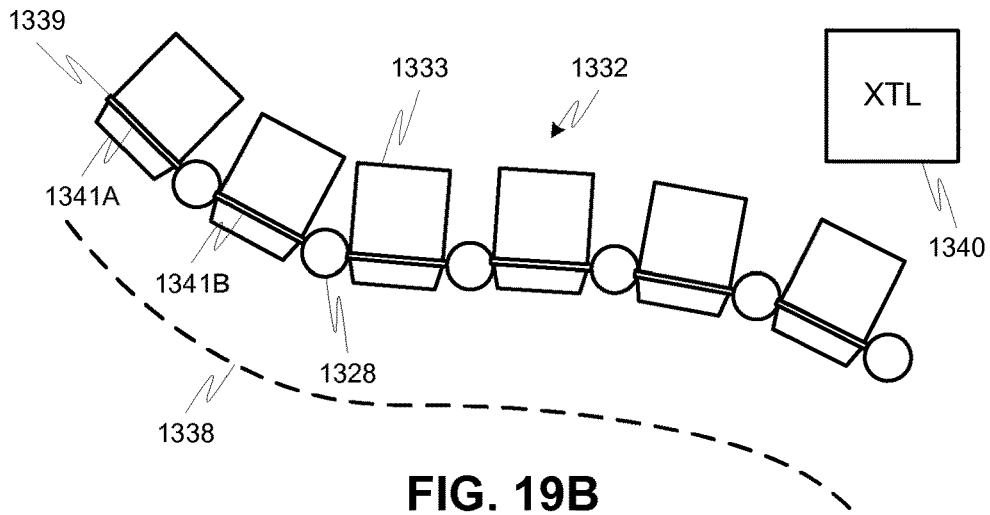
FIG. 19B shows a flexible support, which receives wireless optical tomography imaging probes, that has encoders to determine its own configuration and those of emplaced wireless or wired optical tomography probes.

FIG. 19B shows a flexible support 1339, which receives wireless optical tomography imaging probes 1333. The discussion of FIG. 19A applies to the present configuration in all respects with the exception that in the present embodiment employs a flexible member 1339 that allows an arrangement of attached probe units to be matched to a surface profile 1338. Encoders, which are exemplified in the present embodiment by rotational position encoders 1328, indicate to a controller 1340, the orientations of respective support elements, for example, element 1341A and 1341B, allowing the controller and/or host to estimate the positions of attached probe units 1333. The encoders 1328 may be wired or wirelessly connected to the controller 1340. The Encoders may be resistive, mechanical, or optical encoders and may indicate absolute position or relative position, in the latter case possibly requiring a registration configuration to be established to provide a reference point during configuration for adapting for a particular application. The registration configuration may be, for example, a folded up geometry.

Figure 19C:
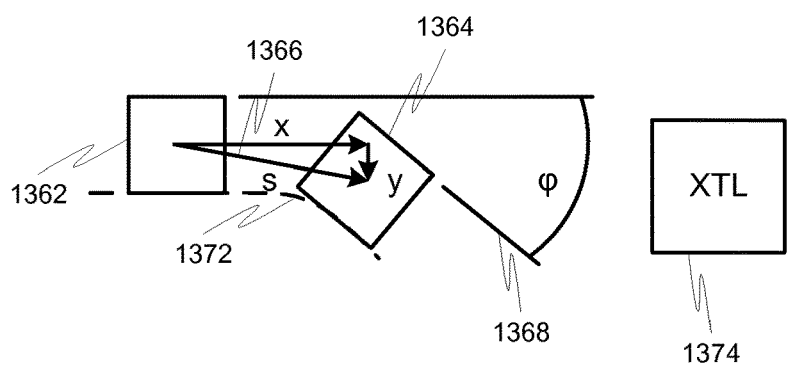
FIG. 19C shows a pair of autonomous wireless optical tomography imaging probes that are controlled wirelessly and whose relative positions and orientations are determined wirelessly so that they can be placed on an arbitrary surface and may receive light signals from each other's sources.

Note that although linear arrays of units are illustrated in FIGS. 19A and 19B, the embodiments may be extended to surface geometries as well. FIG. 19C shows a pair of autonomous wireless optical tomography imaging probes that are controlled wirelessly and whose relative positions and orientations are determined wirelessly so that they can be placed on an arbitrary surface and may receive light signals from each other's sources. The embodiments of 19C may be used with or without a support connecting multiple probe units, two of which are illustrated at 1362 and 1372. A feature that may be employed with any of the described embodiments is to provide a wireless system for determining the positions and orientations of probe units 1362 and 1364. The relative distance and displacements 1366 and 1368 may be generated by transponder signals prompted by a controller 1374. The power for the transponder signals may be generated by the controller in the manner of an RFID tag. The technology for capturing the positions and orientations of the probe units after emplacement on a tissue surface 1372 may include acoustic, optical, or radio systems. A system like that illustrated in FIG. 19C may allow probe units to be installed in garments or other wearable support structures or to be adhesively attached to the skin. Other devices for direct attachment may be used, such as, but not limited to, tape, vacuum connectors, etc. The controller may prompt for position and angle information regularly during motion of the tissue surface 1372. For example, the system may allow the monitoring of blood flow in a moving muscle.

Figure 20:
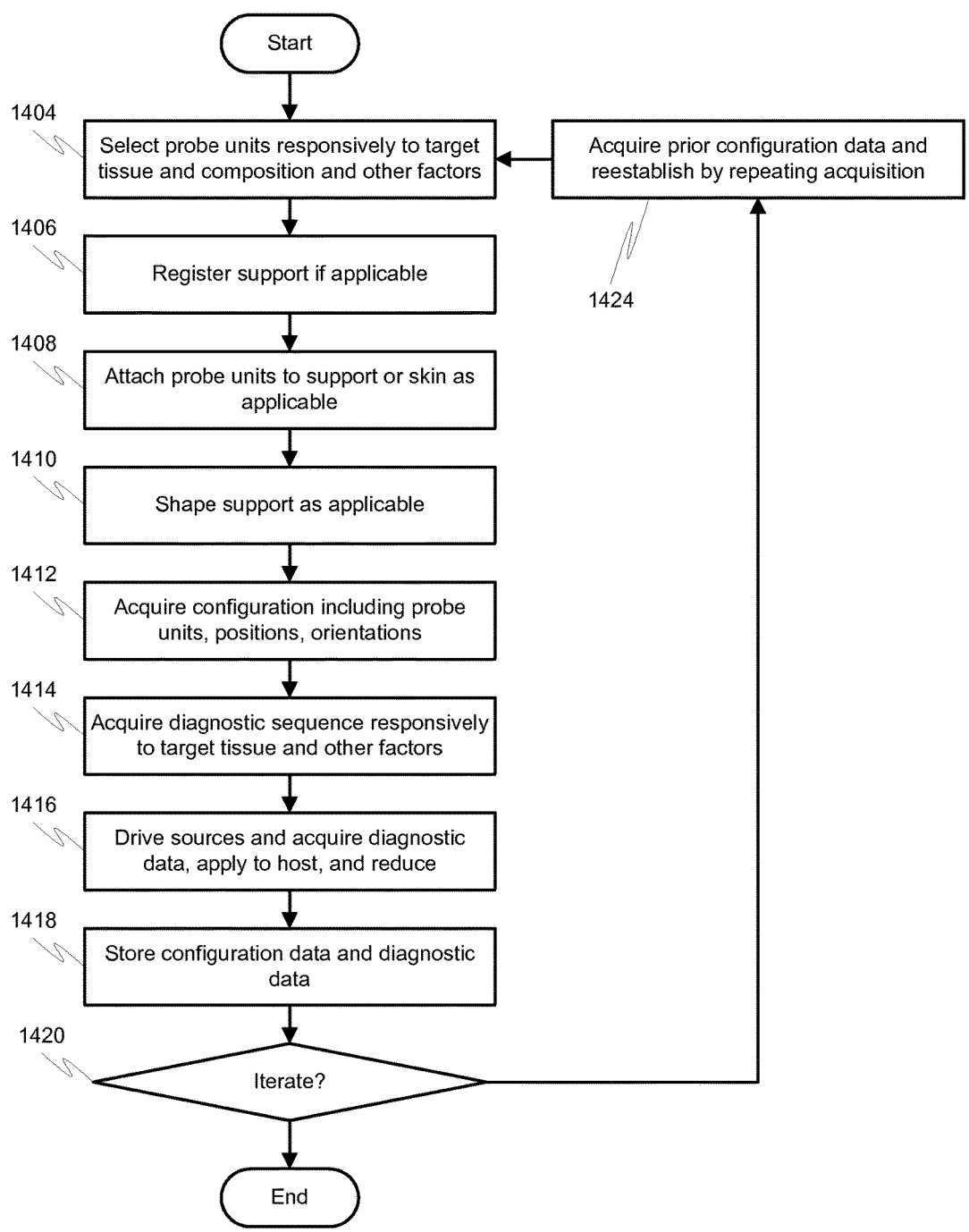
FIG. 20 shows a flow chart defining methods for using optical tomography systems including embodiments described herein.

FIG. 20 is a flow chart illustrating a method that may be used, for example, for the embodiments of FIGS. 19A through 19C. The method begins at 1404 with the selection of probe units which may be selected based on diagnostic criteria or other relevant criteria such as a tissue structure and composition and a kind of diagnostic evaluation to be done. The probe units may be as described with reference to FIGS. 19A through 19C and earlier embodiments may have varying characteristics for example, the number of sources and detectors, the frequencies of sources and detectors, shapes of probe units, modulation domains and speeds of probe units, etc. At 1406, an articulating support such as illustrated in FIG. 19B may require a "home" configuration to register relative displacement encoders. At 1408 the selected probe units are attached to the support or skin of the target body part. At 1410, the support is shaped if applicable to make contact or to position the probe units in a suitable non-contact configuration. At 1412, the configuration data corresponding to the positions and orientations of the probe units is acquired. The configuration data may cover the optical element positions, the orientations, the number of sources and detectors, the control inputs for the sources and control outputs for the detectors etc. The details depend on the embodiments but sufficient information is acquired to provide at least for image generation using optical tomography. At 1414 a diagnostic sequence is loaded into a controller and certain inputs may be prompted for in order to set up a scan acquisition. The sequence may be generated from a profile that was used for making the selection and configuration of 1404, 1408, 1410, and 1412. AT 1416 the probe units are driven by the controller and sample data is acquired, applied to a host computer, and reduced. The reduced data is stored and may be accompanied by configuration data for the diagnostic sequence in 1418. The process may be repeated at a later time whereupon the stored configuration and diagnostic data may be retrieved at 1424 and used to implement another scan sequence.

Note that while the principal embodiment of a probe unit described was based on continuous wave multispectral reflectance mode acquisition, as indicated at various points and noted here, it will be readily apparent that many of the features described herein are applicable to other types of optical tomography systems and methods. In addition, non-contact variants may also be derived from many of the embodiments or features with the substitution of suitable optical elements. For example, sources can be applied to the skin using a remote laser and return signals focused and masked by receiving optics to provide standoff variations of the disclosed embodiments. Note also that many of the embodiments can be extended to conductor-connected variations such as USB wired connections and to optical-path connections such as fiber optical leads. For example, the embodiments of FIGS. 19A through 19C can lend added value to traditional configurations that use optical fiber connections to an embedded system for processing.

While specific examples of transmission of data between the probe and a remote terminal using Bluetooth wireless communication have been described herein, embodiments of the disclosed subject matter are not limited thereto. Rather, other forms of data transmission, whether wireless or wired, are also possible. For example, data transmission between the probe and a remote terminal can be achieved using near field communication. In another example, the imaging probe can be provided with internal memory for storing data obtained by the detectors of the probe during an imaging session. The imaging probe can also include an external connector, where data contained in the internal memory can be transferred to the remote terminal. After the imaging session, or during a break in the imaging session, the imaging probe can be connected to the remote terminal via the external connector for data transfer and processing. For example, the imaging probe can be connected to the remote terminal by a wired connection, such as, but not limited to, a serial cable, Ethernet cable, USB cable, or any other cable.

In still another example, the imaging probe external connector may interface directly with an appropriate receptacle on the remote terminal (e.g., in a docking arrangement) for providing a data and/or power transmission link therebetween. The imaging probe may be provided with a rechargeable battery that is recharged by docking with the remote terminal.

Applications of the disclosed handheld imaging device are not limited to medical applications in general or therapeutic monitoring in particular. Rather, appropriate selection and design of the interrogation wavelengths, source/detector layout, and evolution algorithms can allow the disclosed systems, methods, and devices to be used for other applications as well, such as, but not limited to, use in monitoring material composition or chemical solutions.

It will be appreciated that the methods, processes, and systems described above can be implemented in hardware, hardware programmed by software, software instruction stored on a non-transitory computer readable medium or a combination of the above. For example, the processors described herein can be configured to execute a sequence of programmed instructions stored on a non-transitory computer readable medium. The processors can include, but are not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, or another structured or object-oriented programming language. The sequence of programmed instructions and data associated therewith can be stored in a non-transitory computer-readable medium such as a computer memory or storage device which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

Furthermore, the disclosed methods, processes, systems, and/or algorithms can be implemented by a single processor or by a distributed processor. Further, it should be appreciated that the steps discussed herein can be performed on a single or distributed processor (single and/or multi-core). Also, the methods, processes, systems, and/or algorithms described in the various figures of and for embodiments above can be distributed across multiple computers or systems or can be co-located in a single processor or system. Exemplary structural embodiment alternatives suitable for implementing the methods, processes, systems, and/or algorithms described herein are provided below, but not limited thereto.

The methods, processes, systems, and/or algorithms described herein can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example. Moreover, embodiments of the disclosed methods, processes, systems, and/or algorithms (i.e., computer program product) can be implemented in software executed on a programmed general purpose computer, a special purpose computer, a microprocessor, or the like.

Embodiments of the disclosed methods, processes, systems, and/or algorithms (or their sub-components or modules), can be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, etc. In general, any process capable of implementing the functions or steps described herein can be used to implement embodiments of the methods, processes, systems, algorithms and/or computer program product (software program stored on a non-transitory computer readable medium).

Furthermore, embodiments of the disclosed methods, processes, systems, and/or algorithms can be readily implemented, fully or partially, in software using, for example, object or object-oriented software development environments that provide portable source code that can be used on a variety of computer platforms. Alternatively, embodiments of the disclosed methods, processes, systems, and/or algorithms can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the disclosed methods, processes, systems, and/or algorithms can be implemented in hardware and/or software using any known or later developed systems or structures, devices and/or software by those of ordinary skill in the applicable art from the function description provided herein and with a general basic knowledge of imaging and/or computer programming arts.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for compact optical imaging. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A compact optical imaging system, comprising:
an imaging probe having a plurality of illumination sources and a plurality of detectors disposed on an interrogation face of said probe, each of the illumination sources operating at a respective substantially monochromatic wavelength; and
a processor configured to use signals from the detectors to indicate a degree of contact of the interrogation face with a tissue surface,
wherein the plurality of detectors are disposed at respective detection locations spaced from each other on the interrogation face,
the plurality of illumination sources are disposed at respective illumination locations spaced from each other and said detection locations on the interrogation face, and
the interrogation face is configured to be brought into contact with an object to be imaged such that light from the light sources is scattered and/or partially absorbed by said object prior to detection by one or more of the plurality of detectors.

2. A compact optical imaging system, comprising:
an imaging probe having a plurality of illumination sources and a plurality of detectors disposed on an interrogation face of said probe, each of the illumination sources operating at a respective substantially monochromatic wavelength,
wherein the plurality of detectors are disposed at respective detection locations spaced from each other on the interrogation face,
the plurality of illumination sources are disposed at respective illumination locations spaced from each other and said detection locations on the interrogation face, and
the interrogation face is configured to be brought into contact with an object to be imaged such that light from the light sources is scattered and/or partially absorbed by said object prior to detection by one or more of the plurality of detectors, wherein the imaging probe includes an indicator which notifies a user of the imaging probe of adequate or inadequate contact of the interrogation surface with a tissue surface.

3. The imaging system of claim 2, wherein the interrogation face is substantially planar.

4. The imaging system of claim 2, wherein the interrogation face is curved in at least one dimension.

5. The imaging system of claim 2, wherein the number of detectors on the interrogation face is at least two, and the number of illumination sources on the interrogation face is at least four.

6. The imaging system of claim 2, wherein the illumination sources are arranged in a two-by-two array, and the detectors are arranged along a line perpendicular to a side edge of the array.

7. The imaging system of claim 2, wherein the detectors are semiconductor photodetectors, and the illumination sources are semiconductor light sources.

8. The imaging system of claim 2, wherein the detectors are silicon photodiodes or charge-coupled devices.

9. The imaging system of claim 2, wherein the illumination sources are laser diodes.

10. The imaging system of claim 2, wherein each of the illumination sources operates at a different wavelength.

11. The imaging system of claim 2, wherein the imaging probe includes a head portion and a body portion, the head portion including the illumination sources, the detectors, and the interrogation face, the body portion including a processor and/or electronics therein for controlling the illumination sources and/or processing signals from the detectors.

12. The imaging system of claim 11, wherein the head portion is detachable from the body portion, the head and body portions including respective connectors for connecting said portions together.

13. The imaging system of claim 2, further comprising a remote processor configured to quantitatively determine at least one of absorption, scattering, and chromophore concentration based on signals from the detectors.

14. The imaging system of claim 13, wherein the remote processor is physically disconnected from the imaging probe.

15. The imaging system of claim 14, wherein the imaging probe and the remote processor each include a wireless communication module for transmitting data therebetween.

16. The imaging system of claim 15, wherein the remote processor is configured to use signals from the detectors to indicate a degree of contact of the interrogation face with a tissue surface.

17. The imaging system of claim 2, wherein the indicator provides at least one of a visual indication, audible indication, and tactile indication.

* * * * *